United States Patent
Mohapatra et al.

(10) Patent No.: US 9,493,825 B2
(45) Date of Patent: Nov. 15, 2016

(54) MATERIALS AND METHODS FOR PROFILING MICRORNAS

(75) Inventors: Shyam S. Mohapatra, Lutz, FL (US); Jia-Wang Wang, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 112 days.

(21) Appl. No.: 14/000,517

(22) PCT Filed: Mar. 16, 2012

(86) PCT No.: PCT/US2012/029522
§ 371 (c)(1),
(2), (4) Date: Aug. 20, 2013

(87) PCT Pub. No.: WO2012/129115
PCT Pub. Date: Sep. 27, 2012

(65) Prior Publication Data
US 2014/0004520 A1    Jan. 2, 2014

Related U.S. Application Data

(60) Provisional application No. 61/454,334, filed on Mar. 18, 2011.

(51) Int. Cl.
C12Q 1/68    (2006.01)

(52) U.S. Cl.
CPC ........... *C12Q 1/6851* (2013.01); *C12Q 1/6876* (2013.01)

(58) Field of Classification Search
None
See application file for complete search history.

(56) References Cited

U.S. PATENT DOCUMENTS

| | | |
|---|---|---|
| 2003/0186288 A1 | 10/2003 | Spivack et al. |
| 2004/0014173 A1 | 1/2004 | Anderson et al. |
| 2007/0031857 A1 | 2/2007 | Makarov et al. |
| 2007/0077570 A1 | 4/2007 | Lao et al. |

FOREIGN PATENT DOCUMENTS

| | | |
|---|---|---|
| WO | WO-2009-093254 | 7/2009 |
| WO | WO 2011-103502 | 8/2011 |

OTHER PUBLICATIONS

Tang et al. (2006) Nucl. Acids research vol. 34: No. 2 e9 doi:10.1093/nar/gnj009.*
Costa et al. (2004) Clinical Biochemistry 37 pp: 930-932.*
Valoczi et al. (2004) Nucl. Acids Res. vol. 32, No. 22 e175 doi:10.1093/nar/gnh171.*
Wan G et al., "High-performance quantification of mature microRNAs by real-time RT-PCR using deoxyuridine-incorporated oligonucleotides and hemi-nested primers" *RNA*, 2010, 16(7):1436-1445.
Li J et al., "Real-time Polymerase Chain Reaction MicroRNA Detection Based on Enzymatic Stem-Loop Probes Ligation" *Analytical Chemistry*, 2009, 81(13):5446-5451.
Chen C et al., "Real-time quantification of microRNAs by stem-loop RT-PCR" *Nucleic Acids Research*, 2005, 33(20):e179.
Wark AW et al., "Multiplexed Detection Methods for Profiling microRNA Expression in Biological Samples" *Angewandte Chemie International Edition*, 2008, 47(4):644-652.
Alvarez-Garcia I and Miska EA, "MicroRNA functions in animal development and human disease" *Development*, 2005, 132(21):4653-4662.
Croce CM and Calin GA, "miRNAs, Cancer, and Stem Cell Division" *Cell*, 2005, 122(1):6-7.
Griffiths-Jones S et al., "miRBase: tools for microRNA genomics" *Nucleic Acids Research*, 2008, 36(Database issue):D154-D158.
He L and Hannon GJ, "MicroRNAs: Small RNAs with a Big Role in Gene Regulation" *Nature Reviews Genetics*, 2004, 5(7):522-31.
Nelson PT et al., "Microarray-based, high-throughput gene expression profiling of microRNAs" *Nature Methods*, 2004, 1(2):155-161.
Ro S et al., "A PCR-based method for detection and quantification of small RNAs" *Biochemical and Biophysical Research Communications*, 2006, 351(3):756-763.
Shingara J et al., "An optimized isolation and labeling platform for accurate microRNA expression profiling" *RNA*, 2005, 11(9):1461-1470.
Tang F et al., "MicroRNA expression profiling of single whole embryonic stem cells" *Nucleic Acids Research*, 2006, 34(2):e9.
Varkonyi-Gasic E. et al., "Protocol: a highly sensitive RT-PCR method for detection and quantification of microRNAs" *Plant Methods*, 2007, 3:1-12.
Wang JW and Cheng JQ, "A simple method for profiling miRNA expression" *Methods in Molecular Biology*, 2008, 414:183-90.
Wang H et al., "Direct and sensitive miRNA profiling from low-input total RNA" *RNA*, 2007, 13:151-159.

* cited by examiner

*Primary Examiner* — Suchira Pande
(74) *Attorney, Agent, or Firm* — Saliwanchik Lloyd & Eisenschenk

(57) ABSTRACT

The present invention provides materials and methods for detecting, quantifying, and/or high-throughput-profiling microRNAs. Advantageously, the present invention is more sensitive and specific than other currently-available miRNA qPCR assays. In addition, the present invention is convenient, easy-to-perform, and cost-effective. In one embodiment, the present invention provides a universal primer for reverse transcription of all miRNAs, a universal reverse primer for PCR amplification reaction, and universal probes. In another embodiment, the present invention provides assays that allow simultaneous detection and/or quantification of a plurality of target miRNAs using a single reverse transcription reaction.

5 Claims, 24 Drawing Sheets

| miRNA Assay | Synthetic miRNA target | | | | NTC | Relative detection(%) |
|---|---|---|---|---|---|---|
| | Let-7a | Let-7b | Let-7c | Let-7d | | |
| Let-7a | <u>100.00</u> | 0.00(2) | 0.41(1) | 0.02(3) | 0.00 | |
| Let-7b | 0.00(2) | <u>100.00</u> | 0.00(1) | 1.34(5) | 0.00 | |
| Let-7c | 3.58(1) | 0.30(1) | <u>100.00</u> | 0.00(4) | 0.00 | |
| Let-7d | 0.73(3) | 0.00(5) | 0.00(4) | <u>100.00</u> | 0.00 | |

FIG. 10

| miRNAs | Relative Levels | miRNAs | Relative Levels | miRNAs | Relative Levels |
|---|---|---|---|---|---|
| mmu-let-7a | 2.65 | mmu-miR-17 | 1.80 | miR-202* | - |
| mmu-let-7c | -1.81 | hsa-miR-20a | 2.79 | miR-302 | -3.30 |
| hsa-let-7f-1 | -3.00 | mmu-miR-25 | -1.63 | miR-302b | -1.67 |
| hsa-miR-142-3p | 5.32 | mmu-miR-30d | -2.48 | miR-328 | 1.21 |
| miR-15a | 3.49 | mmu-miR-134 | 59.54 | miR-422b | 18.78 |
| miR-27a | 52.59 | mmu-miR-185 | -1.40 | miR-423 | -10.03 |
| miR-29a | -1.16 | mmu-miR-191 | 2.55 | miR-540 | 147.73 |
| miR-150 | 2.47 | mmu-miR-206 | 115.26 | miR-551a | -3.60 |
| miR-198 | 1.64 | mmu-miR-223 | 9.36 | miR-564 | 39.65 |
| miR-214 | 4.39 | mmu-miR-298 | 1.61 | miR-573 | -89.73 |
| miR-295 | -5.10 | mmu-miR-325 | -5.47 | miR-577 | 1.09 |
| miR-301b | 1.04 | mmu-miR-326 | -3.27 | miR-601 | 3.66 |
| miR-320 | -1.17 | mmu-miR-340-5p | -20.89 | miR-608 | 1.66 |
| miR-370 | -7.43 | mmu-miR-381 | -1.33 | miR-610 | 2.67 |
| miR-470 | -2.82 | mmu-miR-466a-5p | - | miR-611 | -95.42 |
| miR-490 | 8.09 | hsa-miR-493 | 22.06 | miR-637 | 2.50 |
| miR-494 | 1.46 | hsa-miR-527 | -8.05 | miR-638 | 2.23 |
| miR-505 | -5.47 | hsa-miR-542-5p | -9.70 | miR-649 | -14.50 |
| miR-515-3p | 2.24 | hsa-miR-575 | 2.52 | miR-658 | 3.67 |
| miR-513 | -13.32 | hsa-miR-625 | -4.27 | miR-659 | 1.07 |
| miR-584 | -3.61 | mmu-miR-652 | 1.19 | miR-673 | 3.25 |
| miR-588 | -13.81 | hsa-miR-630 | -1.42 | miR-674 | -57.22 |
| miR-671 | 1.61 | hsa-miR-766 | -1.01 | miR-702 | 2.27 |
| miR-680 | 227.11 | mmulet7d | -3.74 | miR-705 | -19.80 |
| miR-690 | -1.95 | mmulet7g | -1.53 | miR-710 | -1.89 |
| miR-709 | 8.70 | mmulet7i | 21.96 | miR-714 | 5.38 |
| miR-711 | -25.93 | miR-15b | 1.40 | miR-721 | - |
| miR-759 | -15.75 | miR-21 | 5.19 | miR-762 | -2.84 |
| miR-760 | -1.18 | miR-23b | 1.44 | miR-768-5p | -1.02 |
| miR-765 | -1.01 | miR-92 | 22.80 | miR-770-3p | 86.51 |
| hsa-miR-518c* | -2.56 | miR-173p | -36.65 | | |
| hsa-miR-363* | -2.32 | miR-202 | 5.65 | | |

FIG. 11

| miRNA targets | miRNA Levels± Stdv | Ratio(miRNA/pre-miRNA) | Student 's t-Test |
|---|---|---|---|
| Let-7a | 119.0385± 23.9421 | 30339.08 | 0.001 |
| pre-Let-7a | 0.0039± 0.0007 | | |
| miR-142 | 96.3132± 10.2997 | 1126.914 | 8.53E-05 |
| pre-miR-142 | 0.0855± 0.0073 | | |
| pre-miR-150 | 0.1286± 0.0179 | | |
| ABI | | | |
| Let-7a | 22.8331± 0.9313 | 1713.398 | 0.000555 |
| pre-Let-7a | 0.0133± 0.0013 | | |
| miR-142 | 42.4295± 1.1968 | 525.9631 | 0.000265 |
| pre-miR-142 | 0.0807± 0.0037 | | |
| pre-miR-150 | n.a | n.a | n.a |

FIG. 12

| miRNA | assay | Synthetic miRNAtarget | | | | NTC | |
|---|---|---|---|---|---|---|---|
| | | Let-7a | Let-7b | Let-7c | Let-7d | | |
| miRNA Primer | Let-7a | 100 | 0.01(2) | 0.081(1) | 0.18(3) | 0 | Relative detection(%) |
| | Let-7b | 0.00(2) | 100 | 0.88(1) | 0.00(5) | 0 | |
| | Let-7c | 0.11 (1) | 0.17 (1) | 100 | 0.00(4) | 0 | |
| | Let-7d | 0.01(3) | 0.00(5) | 0.00(4) | 100 | 0 | |

FIG. 14

| miRNA | Extra Seq | Mature miRNA sequence | Extra Seq | |
|---|---|---|---|---|
| mmu-let-7a | CGCATTGTATGCC | TGAGGTAGTAGGTTGTA-TAGTT | AAA | 39 |
| mmu-let-7c | AGCCCAG | TGAGGTAGTAGGTTGTA-TGGTT | AAA | 32 |
| mmu-let-7b | CTCCTGATT | TGAGGTAGTAGGTTGTG-TGGTT | AAA | 34 |
| mmu-let-7d | CCGAGAGATGAAGA | GAGGTAGTAGGTTGCA-TAGTT | AAA | 36 |
| mmu-let-7e | GCTTGACCAGATTA | TGAGGTAGGAGGTTGTA-TAGTT | AAA | 39 |
| mmu-let-7f | GCACATTGGACGATGATT | GAGGTAGTAGATTGTA-TAGTT | AAA | 43 |
| mmu-let-7g | ACTCCCACCGAT | GAGGTAGTAGTTTGTA-CAGTT | AAA | 35 |
| mmu-let-7i | CAGTGGTTACT | GAGGTAGTAGTTTGTGCT-GTTT | AAA | 35 |

FIG. 15

SEQUENCE LISTING

<160> NUMBER OF SEQ ID NOS: 30

<210> SEQ ID NO 1
<211> LENGTH: 47
<212> TYPE: DNA
<213> ORGANISM: ARTIFICIAL SEQUENCE
<220> FEATURE:
<223> OTHER INFORMATION: UNIVERSAL PRIMER SEQUENCE FOR REVERSE
      TRANSRIPTION OF MIRNAS
<220> FEATURE:
<221> NAME/KEY: misc_feature
<222> LOCATION: (46)..(46)
<223> OTHER INFORMATION: n=a, g or c
<220> FEATURE:
<221> NAME/KEY: misc_feature
<222> LOCATION: (47)..(47)
<223> OTHER INFORMATION: n=a, g, c or t

<400> SEQUENCE: 1
tggctagtta agctcaccag ctcggtacca agcttaacta gccatnn        47

<210> SEQ ID NO 2
<211> LENGTH: 24
<212> TYPE: DNA
<213> ORGANISM: ARTIFICIAL SEQUENCE
<220> FEATURE:
<223> OTHER INFORMATION: A UNIVERSAL REVERSE PRIMER SEQUENCE IN QPCR
      REACTION

<400> SEQUENCE: 2
tggctagtta agctcaccag ctcg                                  24

<210> SEQ ID NO 3
<211> LENGTH: 26
<212> TYPE: DNA
<213> ORGANISM: ARTIFICIAL SEQUENCE
<220> FEATURE:
<223> OTHER INFORMATION: A UNIVERSAL PROBE SEQUENCE

<400> SEQUENCE: 3
tggctagtta agcttggtac cgagct                                26

<210> SEQ ID NO 4
<211> LENGTH: 22
<212> TYPE: DNA
<213> ORGANISM: ARTIFICIAL SEQUENCE
<220> FEATURE:
<223> OTHER INFORMATION: A FORWARD PRIMER SEQUENCE FOR QPCR REACTION

<400> SEQUENCE: 4
tgaggtagta ggttgtatag tt                                    22

<210> SEQ ID NO 5
<211> LENGTH: 22
<212> TYPE: DNA
<213> ORGANISM: ARTIFICIAL SEQUENCE
<220> FEATURE:
<223> OTHER INFORMATION: A FORWARD PRIMER SEQUENCE FOR QPCR REACTION

<400> SEQUENCE: 5
tagcttatca gactgatgtt ga                                    22

<210> SEQ ID NO 6
<211> LENGTH: 23
<212> TYPE: DNA
<213> ORGANISM: ARTIFICIAL SEQUENCE
<220> FEATURE:
<223> OTHER INFORMATION: A FORWARD PRIMER SEQUENCE FOR QPCR REACTION

<400> SEQUENCE: 6
tgtagtgttt cctactttat gga						23

<210> SEQ ID NO 7
<211> LENGTH: 22
<212> TYPE: DNA
<213> ORGANISM: ARTIFICIAL SEQUENCE
<220> FEATURE:
<223> OTHER INFORMATION: A FORWARD PRIMER SEQUENCE FOR QPCR REACTION

<400> SEQUENCE: 7
tctcccaacc cttgtaccag tg						22

<210> SEQ ID NO 8
<211> LENGTH: 24
<212> TYPE: DNA
<213> ORGANISM: ARTIFICIAL SEQUENCE
<220> FEATURE:
<223> OTHER INFORMATION: A FORWARD PRIMER SEQUENCE FOR QPCR REACTION

<400> SEQUENCE: 8
tgaaacatac acgggaaacc tctt						24

<210> SEQ ID NO 9
<211> LENGTH: 22
<212> TYPE: DNA
<213> ORGANISM: ARTIFICIAL SEQUENCE
<220> FEATURE:
<223> OTHER INFORMATION: A FORWARD PRIMER SEQUENCE FOR QPCR REACTION

<400> SEQUENCE: 9
aaaggctagg ctcacaacca aa						22

<210> SEQ ID NO 10
<211> LENGTH: 148
<212> TYPE: DNA
<213> ORGANISM: ARTIFICIAL SEQUENCE
<220> FEATURE:
<223> OTHER INFORMATION: A UNIVERSAL PRIMER SEQUENCE FOR REVERSE
      TRANSCRIPTION OF MIRNAS
<220> FEATURE:
<221> NAME/KEY: misc_feature
<222> LOCATION: (147)..(147)
<223> OTHER INFORMATION: n=a, g or c
<220> FEATURE:
<221> NAME/KEY: misc_feature
<222> LOCATION: (148)..(148)
<223> OTHER INFORMATION: n=a, g, c or t

<400> SEQUENCE: 10
ccatcaatcg tgtgtctcta tggatgctgt cacaacgaca tgtcagcctc tgactccagg		60 atctgtagac gctagctgac atgtcgttgt gacagcatcc atagagacac acgattgatg		120 gttttttttt ttttttttttt tttttttnn						148

<210> SEQ ID NO 11
<211> LENGTH: 25
<212> TYPE: DNA
<213> ORGANISM: ARTIFICIAL SEQUENCE
<220> FEATURE:
<223> OTHER INFORMATION: A UNIVERSAL REVERSE PRIMER SEQUENCE IN QPCR
      REACTION

<400> SEQUENCE: 11
gcctctgact ccaggatctg tagac						25

<210> SEQ ID NO 12
<211> LENGTH: 46
<212> TYPE: DNA
<213> ORGANISM: ARTIFICIAL SEQUENCE
<220> FEATURE:
<223> OTHER INFORMATION: A UBLOCKER SEQUENCE USEFUL ACCORDING TO THE
      PRESENT INVENTION

<400> SEQUENCE: 12
cgacauguca gcuaggucgu ttcgguttca cuaucgcuac gcacag            46

<210> SEQ ID NO 13
<211> LENGTH: 56
<212> TYPE: DNA
<213> ORGANISM: ARTIFICIAL SEQUENCE
<220> FEATURE:
<223> OTHER INFORMATION: A UNIVERSAL PRIMER SEQUENCE FOR REVERSE
      TRANSCRIPTION OF MIRNAS
<220> FEATURE:
<221> NAME/KEY: misc_feature
<222> LOCATION: (55)..(55)
<223> OTHER INFORMATION: n=a, g or c
<220> FEATURE:
<221> NAME/KEY: misc_feature
<222> LOCATION: (56)..(56)
<223> OTHER INFORMATION: n=a, g, c or t

<400> SEQUENCE: 13
cugugcguag cgauagugaa accgaaacga ccuagcugac augucgttttt ttttnn    56

<210> SEQ ID NO 14
<211> LENGTH: 28
<212> TYPE: DNA
<213> ORGANISM: ARTIFICIAL SEQUENCE
<220> FEATURE:
<223> OTHER INFORMATION: A UNIVERSAL REVERSE PRIMER SEQUENCE IN QPCR
      REACTION

<400> SEQUENCE: 14
ctgtgcgtag cgatagtgaa accgaaac                                 28

<210> SEQ ID NO 15
<211> LENGTH: 25
<212> TYPE: DNA
<213> ORGANISM: ARTIFICIAL SEQUENCE
<220> FEATURE:
<223> OTHER INFORMATION: A UNIVERSAL REVERSE PRIMER SEQUENCE IN QPCR
      REACTION

<400> SEQUENCE: 15
cgctgtactc caggatctgt agacg                                    25

<210> SEQ ID NO 16
<211> LENGTH: 15
<212> TYPE: DNA
<213> ORGANISM: ARTIFICIAL SEQUENCE
<220> FEATURE:
<223> OTHER INFORMATION: A UNIVERSAL HYDROLYSIS LNA PROBE SEQUENCE

<400> SEQUENCE: 16
accatcaatc gtgtg                                               15

<210> SEQ ID NO 17
<211> LENGTH: 15
<212> TYPE: DNA
<213> ORGANISM: ARTIFICIAL SEQUENCE
<220> FEATURE:
<223> OTHER INFORMATION: A UNIVERSAL HYDROLYSIS LNA PROBE SEQUENCE

<400> SEQUENCE: 17
ctatggatgc tgtca                                                          15

<210> SEQ ID NO 18
<211> LENGTH: 15
<212> TYPE: DNA
<213> ORGANISM: ARTIFICIAL SEQUENCE
<220> FEATURE:
<223> OTHER INFORMATION: A UNIVERSAL HYDROLYSIS LNA PROBE SEQUENCE

<400> SEQUENCE: 18
cgacatgtca gctag                                                          15

<210> SEQ ID NO 19
<211> LENGTH: 39
<212> TYPE: DNA
<213> ORGANISM: ARTIFICIAL SEQUENCE
<220> FEATURE:
<223> OTHER INFORMATION: A PRIMER SEQUENCE DESIGNED FOR THE MMU-LET-7A
      MIRNA

<400> SEQUENCE: 19
cgcattgtta tgcctgaggt agtaggttgt atagttaaa                                 39

<210> SEQ ID NO 20
<211> LENGTH: 32
<212> TYPE: DNA
<213> ORGANISM: ARTIFICIAL SEQUENCE
<220> FEATURE:
<223> OTHER INFORMATION: A PRIMER SEQUENCE DESIGNED FOR THE MMU-LET-7C
      MIRNA

<400> SEQUENCE: 20
agcccagtga ggtagtaggt tgtatggtta aa                                       32

<210> SEQ ID NO 21
<211> LENGTH: 34
<212> TYPE: DNA
<213> ORGANISM: ARTIFICIAL SEQUENCE
<220> FEATURE:
<223> OTHER INFORMATION: A PRIMER SEQUENCE DESIGNED FOR TEH MMU-LET-7B
      MIRNA

<400> SEQUENCE: 21
ctcctgattt gaggtagtag gttgtgtggt taaa                                     34

<210> SEQ ID NO 22
<211> LENGTH: 36
<212> TYPE: DNA
<213> ORGANISM: ARTIFICIAL SEQUENCE
<220> FEATURE:
<223> OTHER INFORMATION: A PRIMER SEQUENCE DESIGNED FOR THE MMU-LET-7D
      MIRNA

<400> SEQUENCE: 22
ccgagagatg aagaggtagt aggttgcata gttaaa                                   36

<210> SEQ ID NO 23
<211> LENGTH: 39
<212> TYPE: DNA
<213> ORGANISM: ARTIFICIAL SEQUENCE
<220> FEATURE:
<223> OTHER INFORMATION: A PRIMER SEQUENCE DESIGNED FOR THE MMU-LET-7E
      MIRNA

<400> SEQUENCE: 23
gcttgaccag attatgaggt aggaggttgt atagttaaa            39

<210> SEQ ID NO 24
<211> LENGTH: 43
<212> TYPE: DNA
<213> ORGANISM: ARTIFICIAL SEQUENCE
<220> FEATURE:
<223> OTHER INFORMATION: A PRIMER SEQUENCE DESIGNED FOR THE MMU-LET-7F
      MIRNA

<400> SEQUENCE: 24
gcacattgga cgatgatttg aggtagtaga ttgtatagtt aaa        43

<210> SEQ ID NO 25
<211> LENGTH: 35
<212> TYPE: DNA
<213> ORGANISM: ARTIFICIAL SEQUENCE
<220> FEATURE:
<223> OTHER INFORMATION: A PRIMER SEQUENCE DESIGNED FOR THE MMU-LET-7G
      MIRNA

<400> SEQUENCE: 25
actccaccga tgaggtagta gtttgtacag ttaaa                35

<210> SEQ ID NO 26
<211> LENGTH: 35
<212> TYPE: DNA
<213> ORGANISM: ARTIFICIAL SEQUENCE
<220> FEATURE:
<223> OTHER INFORMATION: A PRIMER SEQUENCE DESIGNED FOR THE MMU-LET-7I
      MIRNA

<400> SEQUENCE: 26
cagtggttac tgaggtagta gtttgtgctg ttaaa                35

<210> SEQ ID NO 27
<211> LENGTH: 31
<212> TYPE: DNA
<213> ORGANISM: ARTIFICIAL SEQUENCE
<220> FEATURE:
<223> OTHER INFORMATION: POLY(A) SEQUENCE
<220> FEATURE:
<221> NAME/KEY: misc_feature
<222> LOCATION: (31)..(31)
<223> OTHER INFORMATION: n=a, g, c or t

<400> SEQUENCE: 27
aaaaaaaaaa aaaaaaaaaa aaaaaaaaaa n                    31

<210> SEQ ID NO 28
<211> LENGTH: 26
<212> TYPE: DNA
<213> ORGANISM: ARTIFICIAL SEQUENCE
<220> FEATURE:
<223> OTHER INFORMATION: POLY(T) SEQUENCE
<220> FEATURE:
<221> NAME/KEY: misc_feature
<222> LOCATION: (1)..(1)
<223> OTHER INFORMATION: n=a, g or c

<400> SEQUENCE: 28
nttttttttt tttttttttt tttttt                          26

```
<210> SEQ ID NO 29
<211> LENGTH: 28
<212> TYPE: DNA
<213> ORGANISM: ARTIFICIAL SEQUENCE
<220> FEATURE:
<223> OTHER INFORMATION: POLY(A) SEQUENCE
<220> FEATURE:
<221> NAME/KEY: misc_feature
<222> LOCATION: (28)..(28)
<223> OTHER INFORMATION: n=a, g, c or t

<400> SEQUENCE: 29
aaaaaaaaaa aaaaaaaaaa aaaaaaan                                          28

<210> SEQ ID NO 30
<211> LENGTH: 25
<212> TYPE: DNA
<213> ORGANISM: ARTIFICIAL SEQUENCE
<220> FEATURE:
<223> OTHER INFORMATION: POLY(A) SEQUENCE

<400> SEQUENCE: 30
tttttttttt tttttttttt ttttt                                             25
```

MATERIALS AND METHODS FOR PROFILING MICRORNAS

CROSS-REFERENCE TO RELATED APPLICATIONS

The present application is the National Stage of International Application No. PCT/US2012/029522, filed Mar. 16, 2012, which claims the benefit of U.S. Provisional Application Ser. No. 61/454,334, filed Mar. 18, 2011, each of which is hereby incorporated by reference herein in its entirety, including any figures, tables, or drawings.

GOVERNMENT SUPPORT

This invention was made with government support under Grant Number N00014-09-1-1008 awarded by the Office of Naval Research. The government has certain rights in the invention.

BACKGROUND OF THE INVENTION

MicroRNAs (miRNAs), typically 18 to 25 nt in length, are non-protein-coding RNAs that can inhibit the translation of target mRNAs (Croce and Calin. 2005. miRNAs, cancer, and stem cell division. *Cell* 122(1): 6-7). miRNAs directly or indirectly regulate a wide range of genes, and are involved in a remarkable spectrum of biological pathways including cell development, proliferation and apoptosis (He and Hannon. 2004. MicroRNAs: small RNAs with a big role in gene regulation. *Nat Rev Genet* 5(7): 522-31, Alvarez-Garcia and Miska. 2005. MicroRNA functions in animal development and human disease. *Development* 132(21): 4653-62). As of September 2009, 10883 miRNA entries from vertebrates, flies, worms, plants, and viruses, including 721 human miRNAs and 579 mouse miRNAs, have been annotated (miRBase, Release 14) in the Sanger Institute miRNA sequence database (Griffiths-Jones, Saini, van Dongen and Enright. 2008. miRBase: tools for microRNA genomics. *Nucleic Acids Res* 36(Database issue): D154-8); the function of many miRNAs is unknown.

Materials and Methods that can detect and quantify miRNAs with high sensitivity and specificity are useful. Cellular miRNA profiles can offer insights into gene expression, and allow the determination of the species, tissue types, and developmental stages of tissue samples. Further, the detection and quantification of miRNAs can lead to the discovery of novel, miRNA-based diagnostic/prognostic biomarkers and therapeutic agents.

However, detection of mature miRNAs is difficult due to several reasons. First, miRNAs are difficult to detect because they are relatively short nucleic acid molecules (on average, only about 22 bases in length). In addition, these short sequences can be present in sequences other than mature miRNA, such as pre-miRNA, pri-miRNA, genomic DNA and mRNA. Further, it is difficult to distinguish miRNAs within the same family, as these miRNAs usually differ from each other only in terms of one or a few nucleotides. Moreover, the melting temperatures (Tm) of miRNAs can vary greatly, from about 55° C. to 90° C.

At present, although a wide spectrum of miRNA detection techniques have been developed, there is a lack of high-throughput profiling assays that can sensitively and specifically detect miRNAs. Conventional techniques for miRNA profiling include Northern hybridization, cloning, and microarray analysis. (Wang, Ach and Curry. 2007. Direct and sensitive miRNA profiling from low-input total RNA. *RNA* 13(1): 151-9, Wang and Cheng. 2008. A simple method for profiling miRNA expression. *Methods Mol Biol* 414: 183-90, Shingara, Keiger, Shelton, Laosinchai-Wolf, Powers, Conrad, Brown and Labourier. 2005. An optimized isolation and labeling platform for accurate microRNA expression profiling. *RNA* 11(9): 1461-70, Nelson, Baldwin, Scearce, Oberholtzer, Tobias and Mourelatos. 2004. Microarray-based, high-throughput gene expression profiling of microRNAs. *Nat Methods* 1(2): 155-61). These techniques are not as sensitive or specific, when compared to quantitative real-time reverse transcription PCR (qRT-PCR).

Several qRT-PCR-based methods have been developed for detecting and quantifying miRNAs (Li, Yao, Huang, Wang, Sun, Fan, Chang, Li, Wang and Xi. 2009. Real-time polymerase chain reaction microRNA detection based on enzymatic stem-loop probes ligation. *Anal Chem* 81(13): 5446-51, Varkonyi-Gasic, Wu, Wood, Walton and Hellens. 2007. Protocol: a highly sensitive RT-PCR method for detection and quantification of microRNAs. *Plant Methods* 3: 12, Ro, Park, Jin, Sanders and Yan. 2006. A PCR-based method for detection and quantification of small RNAs. *Biochem Biophys Res Commun* 351(3): 756-63). The current reverse transcriptase quantitative polymerase chain reaction assays (RT-qPCR), which use SYBR Green, are lacking in specificity and sensitivity, as SYBR Green detects all forms of nucleic acids, including double-stranded DNA, double-stranded RNA, single-stranded RNA and DNA, although the detection sensitivity of double-stranded RNA, single-stranded RNA and DNA is lower than that of double-stranded DNA.

The most frequently used qRT-PCR-based method, developed by Chen et al. (Chen, Ridzon, Broomer, Zhou, Lee, Nguyen, Barbisin, Xu, Mahuvakar, Andersen, Lao, Livak and Guegler. 2005. Real-time quantification of microRNAs by stem-loop RT-PCR. *Nucleic Acids Res* 33(20): e179), includes two main steps: reverse transcription of miRNAs using stem-loop RT primers, followed by a TaqMan® PCR analysis.

However, the Chen et al. method has several limitations. According to Chen et al., profiling each target miRNA requires a target-specific TaqMan® probe and a target-specific RT primer. As a result, the cost of making hundreds of target-specific probes and RT primers during miRNA screening tests can be prohibitive. In addition, the Chen et al. method is procedurally complex. Profiling each miRNA requires an RT reaction; otherwise, if only one RT reaction is performed, all miRNA-specific RT primers need to be mixed together. Further, hundreds of target-miRNA specific TaqMan® probes need to be added separately in order to detect or quantify miRNA. Moreover, RT primers used in the Chen et al. method only have a 6-nt-sequence that base-pairs with the target miRNAs. As a result, the RT primers may hybridize to, and prime, other RNAs during the RT reaction (Tang, Hajkova, Barton, Lao and Surani. 2006. MicroRNA expression profiling of single whole embryonic stem cells. *Nucleic Acids Res* 34(2):e9). Accordingly, improved methods for profiling miRNAs are needed.

BRIEF SUMMARY OF THE INVENTION

The present invention provides materials and methods for detecting, quantifying, and/or profiling microRNAs. Advantageously, the present invention is sensitive, specific, convenient, and cost-effective. Further, the present invention can detect mature miRNA in a sample that comprises non-mature miRNA nucleic acids (such as one or more of genomic DNA, pre-miRNA, pri-miRNA and mRNA, and cDNAs thereof) that also comprise the target miRNA sequence.

In one aspect, materials for detecting, quantifying, and/or profiling microRNAs comprise: a universal primer for reverse transcription of miRNAs, a universal reverse primer for PCR amplification reaction, and a universal probe (multiple universal probes can be used to increase the detection sensitivity). Also provided are reagents and kits for detecting, quantifying, and/or profiling miRNAs.

In some embodiments, the universal primer for reverse transcription is an oligonucleotide comprising: a $(dT)_n$ sequence flanked by a stem-looped universal adaptor sequence, wherein "n" is an integer ranging from 8 to 50, wherein the universal primer comprises at least two nucleotides adjacent to the 3' end of the $(dT)_n$ sequence, and the nucleotide immediately adjacent to the $(dT)_n$ sequence is not T, and wherein the universal adaptor sequence near the 5' end of the $(dT)_n$ sequence forms a stem-loop structure by base-pairing.

In one embodiment, the universal reverse primer is an oligonucleotide comprising a sequence that is, or base-pairs with, at least part of the adaptor sequence near the 5' end of the $(dT)_n$ sequence. In one embodiment, the universal probe comprises a sequence that is, or base-pairs with, at least part of the adaptor sequence near the 5' end of the $(dT)_n$ sequence.

In some embodiments, the universal primer for reverse transcription comprises SEQ ID NO: 1. In some embodiments, the universal reverse primer for PCR amplification comprises SEQ ID NO: 2. In some embodiments, the universal probe comprises SEQ ID NO: 3.

In another aspect, the present invention provides assays for detecting, quantifying, and/or profiling miRNAs. In one embodiment, the present invention can detect a plurality of target miRNAs using one reverse transcription reaction and one qPCR reaction. Advantageously, the present invention can detect, quantify, and/or profile miRNAs at a level of about 1 pg of total RNA.

In one embodiment, the method for detecting, quantifying, and/or profiling a target miRNA comprises:

a) contacting a sample comprising miRNAs with an effective amount of poly(A)polymerase molecules to yield 3' end-polyadenylated miRNA molecules;

b) contacting the sample with an effective amount of a universal primer for reverse transcription and reverse transcriptases, and reverse transcribing the polyadenylated miRNA molecules to yield corresponding c-DNA molecules; and c) contacting the sample with an effective amount of a universal reverse primer and a forward primer, and amplifying the corresponding c-DNA molecules using an amplification reaction (e.g., PCR).

In a further embodiment, the present invention uses Surveyor nuclease and/or single strand endonucleases that remove mis-matches caused by misprinting to enhance specificity and/or single strand endonucleases such as Exonuclease I that remove single-stranded DNA such as excess primers. In another embodiment, the present invention uses uracil-DNA Glycosylase (UDG) and/or dUTP to enhance specificity.

In some embodiments, a plurality of probes is used for detection and/or quantification of target miRNAs. In some embodiments, the universal probe comprises one or more locked-nucleic acids (LNAs).

In one embodiment, the forward primer comprises the target-miRNA sequence, one or more additional nucleotides (such as adenine molecules) attached to the 3' end of the target mature miRNA sequence, and one or more additional nucleotides attached to the 5' end of the target mature miRNA sequence.

BRIEF DESCRIPTION OF THE DRAWINGS

FIG. 10 shows that the UQmiR miRNA qPCR assay of the present invention discriminates mouse Let-7 miRNA family members. Four closely-related let-7 family members (let-7a to let-7d) were used in the assay. Relative miRNA detection percentages (%) to the perfectly matched targets were calculated based on Cq values. A total of 7.85E8 copies of synthetic RNA were added to the RT reaction. The numbers in parentheses indicate the difference in bases between each pair of miRNAs.

FIG. 11 shows relative plasma miRNA expression levels of human plasma miRNAs pooled from five normal volunteers measured by the RT-qPCR miRNA assay of the present invention. The results show that the present RT-qPCR miRNA assay can sensitively and specifically detect 88 out of 94 miRNAs (those miRNAs have high expression levels in mouse spleens from the dot blot array results) in a sample that only contains 0.8 ml of plasma for each miRNA.

FIG. 12 shows that the UQmiR miRNA qPCR assay of the present invention discriminates mature miRNAs from pre-miRNAs. Mature miRNA-specific primers were used to detect mature miRNA and pre-miRNA sequences. A total of 7.85E8 copies of synthetic pre-miR-142 and pre-miR-150 were added to the RT reaction. The results show that mature miRNA-specific primers do not amply pre-miRNA. The folds of discrimination are over one thousand times.

FIG. 14 shows discrimination UDG assay of mouse Let-7 miRNA family members. Four closely related let-7 family members (from let-7a to let-7d) were included in the assay. Relative miRNA detection percentages (%) to the perfectly matched targets were calculated based on Cq values. A total of 7.85E8 copies of synthetic RNA were added to the RT reaction. The numbers in parentheses indicate different bases between each pair of the miRNAs. RT primer that contains multiple Uracil nucleotides were used (LUTVN RT primer and Ublocker in Table 2), and after the double strand cDNA synthesis, a mixture of Uracil DNA glycosylase (UDG) and the DNA glycosylase-lyase Endonuclease VIII was used to remove LUTVN RT primer and Ublocker. Very low levels of non-specific signal were observed, ranging from 0 to 0.18% (0 to 0.3, Chen et al. method) for miRNAs with 2-5 mismatched bases and only 0.11 to 0.88% (0.1 to 3.7, Chen et al. method) for the miRNAs that differed by a single nucleotide.

FIG. 15 illustrates an embodiment of UQmiR primers designed for the Let-7 miRNA family. UQmiR primers are designed so that they have minimal homology between each other, especially within a miRNA family, to increase UQmiR specificity between homologous miRNA sequences. The number of different bases between each miRNA sequence is greatly increased from one or a few. The primers in FIG. 15 are mmu-let-7a (SEQ ID NO:19); mmu-let-7c (SEQ ID NO:20); mmu-let-7b (SEQ ID NO:21); mmu-let-7d (SEQ ID NO:22); mmu-let-7e (SEQ ID NO:23); mmu-let-7f (SEQ ID NO:24); mmu-let-7g (SEQ ID NO:25); and mmu-let-7i (SEQ ID NO:26).

BRIEF DESCRIPTION OF THE SEQUENCES

SEQ ID NO: 1 is a universal primer sequence for reverse transcription of miRNAs (RTUloop).

SEQ ID NO: 2 is a universal reverse primer sequence in qPCR reaction (QRTU).

SEQ ID NO: 3 is a universal probe sequence (miRU probe).

SEQ ID NO: 4 is a forward primer sequence for qPCR reaction (Let-7a).

SEQ ID NO: 5 is a forward primer sequence for qPCR reaction (miR-21).

SEQ ID NO: 6 is a forward primer sequence for qPCR reaction (miR-142).

SEQ ID NO: 7 is a forward primer sequence for qPCR reaction (miR-150).

SEQ ID NO: 8 is a forward primer sequence for qPCR reaction (miR-494).

SEQ ID NO: 9 is a forward primer sequence for qPCR reaction (mmu-miR-690).

SEQ ID NO: 10 is a universal primer sequence for reverse transcription of miRNAs.

SEQ ID NO: 11 is a universal reverse primer sequence in qPCR reaction.

SEQ ID NO: 12 is a Ublocker sequence useful according to the present invention.

SEQ ID NO: 13 is a universal primer sequence for reverse transcription of miRNAs.

SEQ ID NO: 14 is a universal reverse primer sequence in qPCR reaction.

SEQ ID NO: 15 is a universal reverse primer sequence in qPCR reaction.

SEQ ID NO: 16 is a universal hydrolysis LNA probe sequence.

SEQ ID NO: 17 is a universal hydrolysis LNA probe sequence.

SEQ ID NO: 18 is a universal hydrolysis LNA probe sequence.

SEQ ID NO: 19 is a primer sequence designed for the mmu-let-7a miRNA useful according to the present invention (FIG. 15).

SEQ ID NO: 20 is a primer sequence designed for the mmu-let-7c miRNA useful according to the present invention (FIG. 15).

SEQ ID NO: 21 is a primer sequence designed for the mmu-let-7b miRNA useful according to the present invention (FIG. 15).

SEQ ID NO: 22 is a primer sequence designed for the mmu-let-7d miRNA useful according to the present invention (FIG. 15).

SEQ ID NO: 23 is a primer sequence designed for the mmu-let-7e miRNA useful according to the present invention (FIG. 15).

SEQ ID NO: 24 is a primer sequence designed for the mmu-let-7f miRNA useful according to the present invention (FIG. 15).

SEQ ID NO: 25 is a primer sequence designed for the mmu-let-7g miRNA useful according to the present invention (FIG. 15).

SEQ ID NO: 26 is a primer sequence designed for the mmu-let-7i miRNA useful according to the present invention (FIG. 15).

Figure 1:
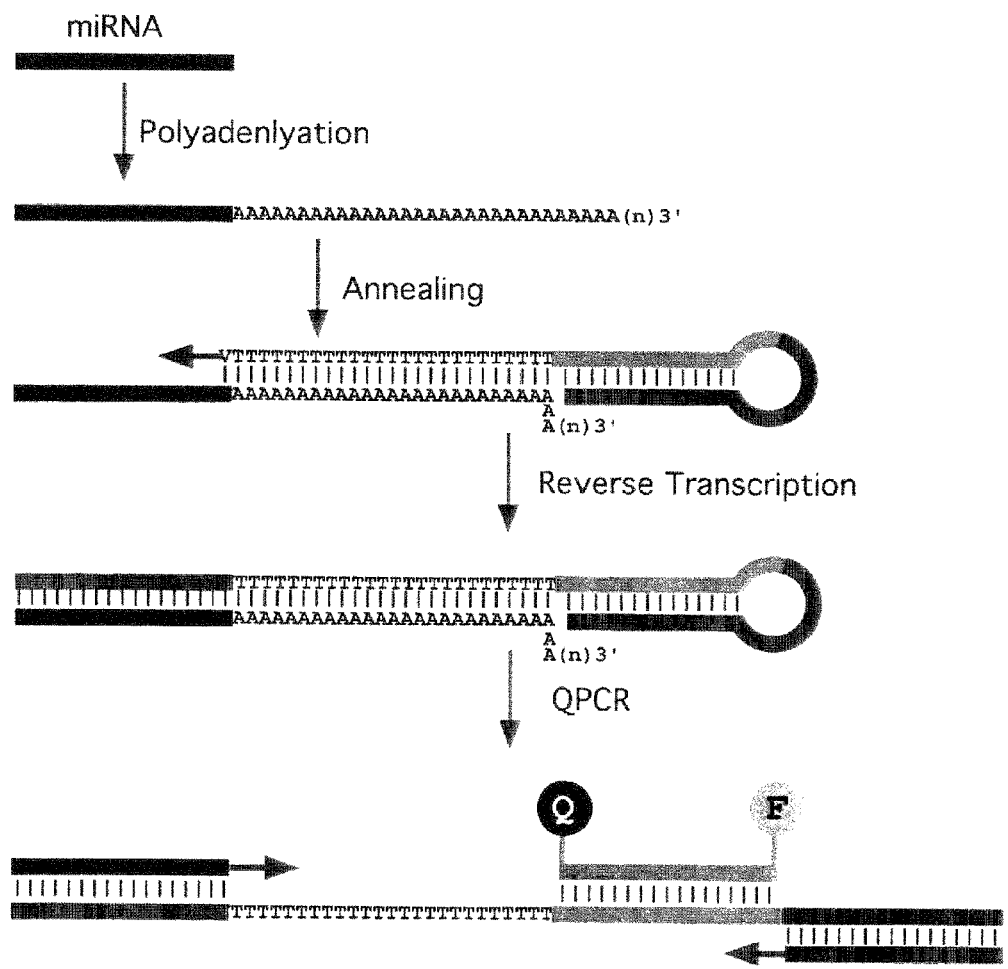
FIG. 1 is a schematic illustration of an embodiment of the qRT-PCR assay for profiling miRNA, using a universal TaqMan® probe and a universal RT primer. Briefly, miRNAs are polyadenylated using poly(A)polymerase molecules. The poly(A)-tailed miRNAs are then reverse-transcribed into cDNAs using a universal primer comprising oligo dTs flanked by a stem-loop adaptor sequence. Finally, the cDNAs are amplified by qRT-PCRs using a mature target miRNA sequence as the forward primer and a universal reverse primer (QRTU). In one embodiment, a universal TaqMan® probe is used to detect the amplification product. Q=Quencher, such as IABlk_FQ (Iowa Black™ FQ), F=Fluorescent Dye, such as FAM (6-carboxyfluorescein). SEQ ID NOS: 27-30 are sequences shown in FIG. 1.

SEQ ID NO: 27 is a poly(A) sequence (FIG. 1).

SEQ ID NO: 28 is a poly(T) cDNA sequence reverse-transcribed from a poly(A) sequence (FIG. 1).

SEQ ID NO: 29 is a poly(A) sequence (FIG. 1).

SEQ ID NO: 30 is a poly(A) sequence (FIG. 1).

DETAILED DISCLOSURE OF THE INVENTION

The present invention provides materials and methods for detecting, quantifying, and/or profiling microRNAs. The present invention uses a reverse transcription reaction and a PCR amplification reaction. In one embodiment, the present invention uses a universal probe, such as a TaqMan® probe, and a universal RT-primer (UPR).

Advantageously, the UQmiR qRT-PCR assay can be sensitive, specific, convenient, and cost-effective. In one embodiment, the present invention uses a universal probe (such as a TaqMan®) and a universal RT primer (UPR). In a preferred embodiment, the present invention can detect a plurality of target miRNAs using one RT reaction and a single universal probe (multiple universal probes may be used to increase the detection sensitivity). Advantageously, the present invention allows detection and quantification of miRNAs in as little as 1 pg total RNA. Further, the present invention can detect mature miRNA in a sample that contain non-mature miRNA nucleic acids (such as genomic DNA, pre-miRNA, pri-miRNA and mRNA, and cDNAs thereof) that also comprise the target miRNA sequence. For instance, genomic DNA and mRNA in total RNA samples produce no or little detectable signals.

Total RNA used in the present invention can be obtained from simple extraction methods, such as, Trizol extraction. Total RNA samples used in the present invention need not be treated with DNases or undergo small RNA fractionation or purification, which are not only labor intensive procedures, but also may result in significant loss of input miRNAs.

The miRNA UQmiR qRT-PCR assay of the present invention has two major advantages when compared to the conventional miRNA stein-loop qRT-PCR methods (such as the Chen et al. method). First, a highly specific universal poly (T) primer, for example with a stretch of 25Ts, is used to prime the RT reaction for detection of all target miRNAs. In contrast, the conventional methods use a stem-loop RT primer that has a 6 nt sequence specific to each target miRNA sequence. For example, the 25Ts poly (T) sequence in the universal primer theoretically appears only once in a random sequence of 1.1259E+15 bps, while the 6 nt-sequence in the miRNA-specific primer appears 652962 times in a random sequence of the mouse genomic size. Further, the 6 nt, target-miRNA-specific primer used in the prior art methods is not genome-wide specific; It can not only prime the target miRNAs, but also prime other RNAs that have the Ent sequences. Further, using the prior art primers requires lower temperature (16° C.) for RT reaction (Chen, Ridzon, Broomer, Zhou, Lee, Nguyen, Barbisin, Xu, Mahuvakar, Andersen, Lao, Livak and Guegler. 2005. Real-time quantification of microRNAs by stem-loop RT-PCR. *Nucleic Acids Res* 33(20): e179). Therefore, the present invention can greatly increase the priming specificity during reverse transcription, since only RNAs that have poly (A) tails can be reversely transcribed. The decrease of non-specificity in the RT reaction increases the sensitivity of the qRT-PCR assay.

Moreover, the present invention can use a universal probe (such as a universal TaqMan® probe) for the detection and qualification of a plurality of miRNAs. In contrast, the conventional methods require target-miRNA-specific Taq- Man® probes, where each probe can only detect one target miRNA. In addition, conventional methods require that each target-specific probe need to be individually added each time. The present invention also embodies the use of multiple universal probes to increase the detection sensitivity.

Figure 5:
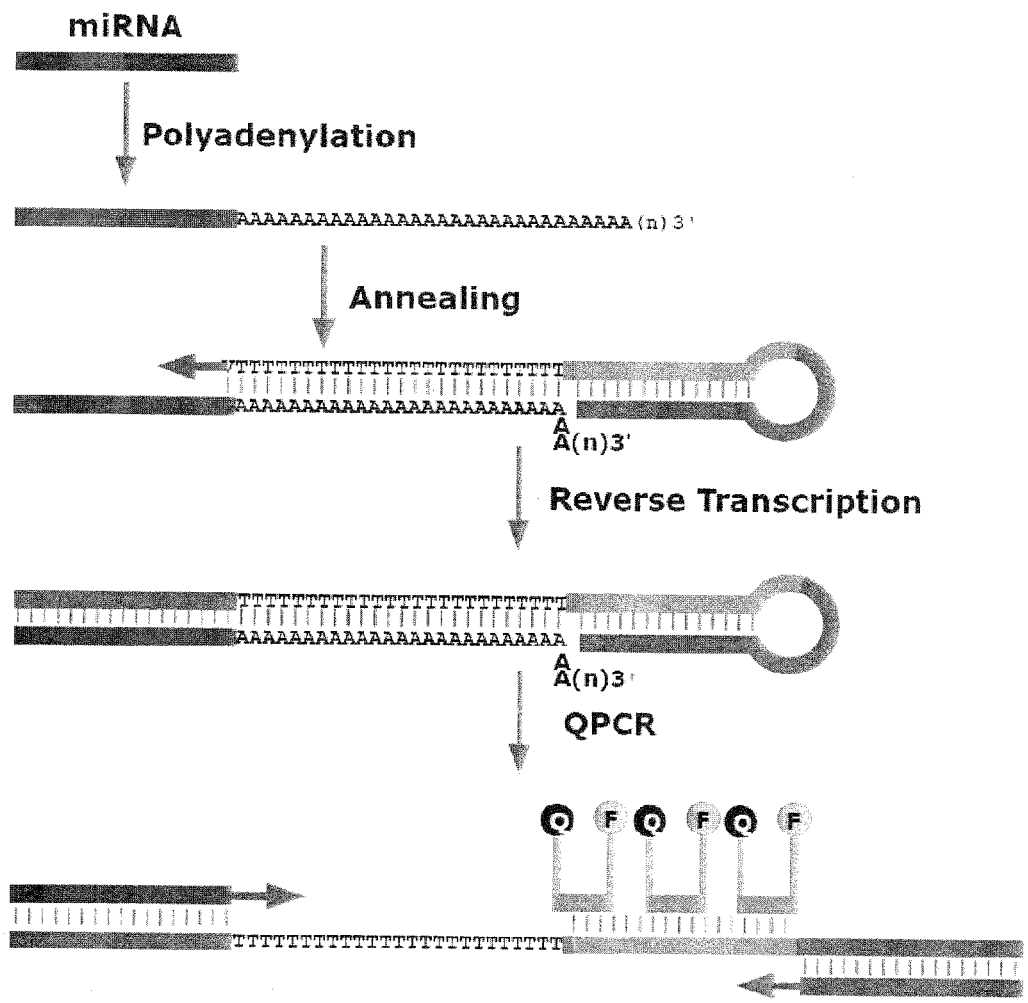
FIG. 5 is a schematic illustration of an embodiment of the UQmiR quantitative real-time PCR assay for profiling miR-NAs, using one or more universal hydrolysis probes and a universal RT primer. Briefly, miRNAs are polyadenylated using poly(A)polymerase molecules. The poly(A)-tailed miRNAs are then reverse-transcribed into cDNAs using a universal primer comprising oligo-dTs flanked by a stem-loop adaptor sequence (see Table 2). Finally, the cDNAs are amplified by RT-qPCR using a UQmiR forward primer comprising the target mature miRNA sequence and a universal reverse primer (QRTU). Multiple universal hydrolysis probes can be used to sensitively detect the amplicons. Q quencher, (e.g., IABlk_FQ); F=fluorescent dye, (FAM).
Figure 6:
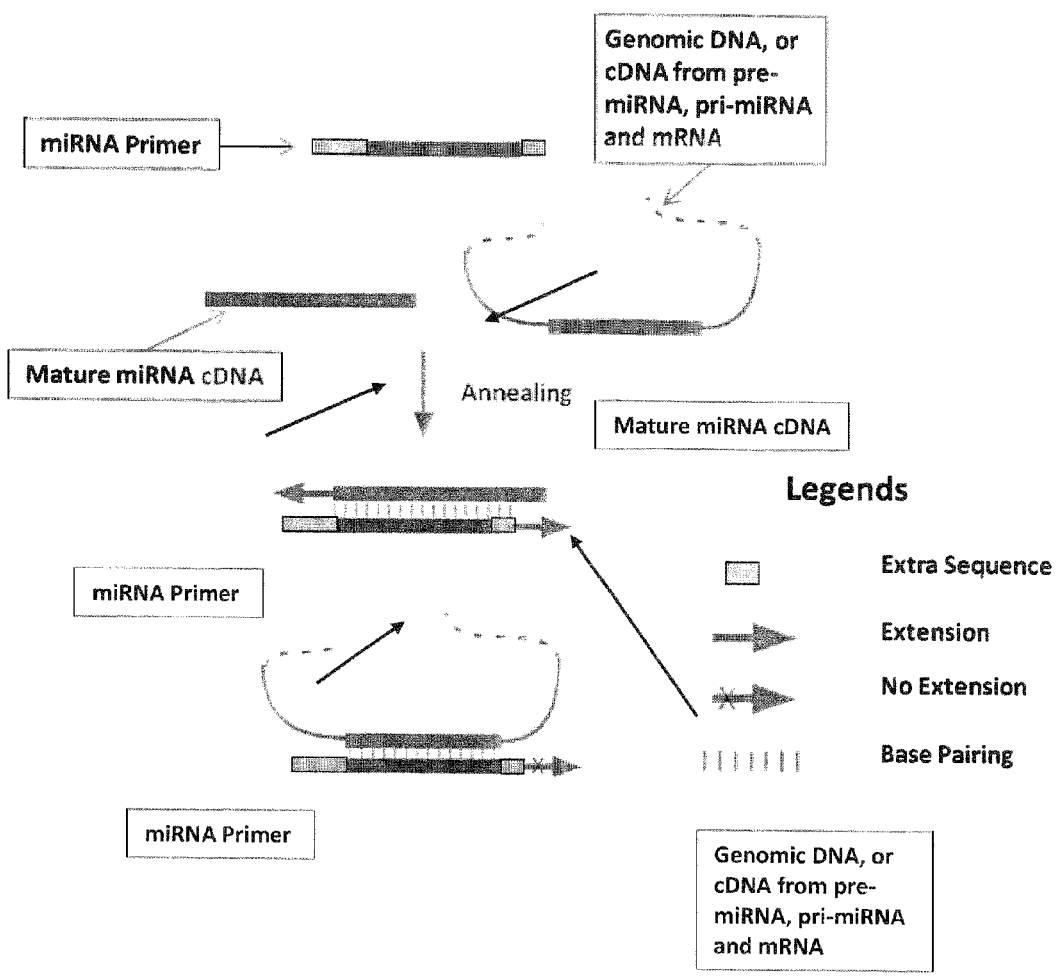
FIG. 6 illustrates that the UQmiR miRNA RT-qPCR assay sensitively and specifically amplifies mature miRNAs. In one embodiment, the forward primer (UQmiR primer) of the amplification reaction comprises the target mature miRNA sequence and additional sequences attached to the 5'- and 3'-ends of the mature miRNA sequence. The UQmiR-primer is annealed to the cDNA of the target mature miRNA, and extension occurs at both ends of the primer-cDNA complex; however, unlike the complex formed by the UQmiR-primer and the mature miRNA cDNA, there is no extension at both ends of the complex formed by the UQmiR-primer and other DNA molecules. Attachment of additional sequences at the 5'- and 3' ends of the target mature miRNA sequence also results in higher Tm for the UQmiR primer. After extension reaction by a DNA polymerase, the Tm of the cDNA template from a specific miRNA may be increased. Advantageously, the UQmiR primer does not anneal to, or has a low probability of annealing to, the nucleic acid molecules other than cDNA from mature miRNA (such as, genomic DNA, cDNAs of pre-miRNA, pri-miRNA and mRNA) that contain the mature miRNA sequence; Due to lower homology between the UQmiR primer and those molecules, the complex formed by them is less stable than the complex formed by the UQmiR primer and the cDNA from specific mature miRNA.

In a further embodiment, the present invention provides a RT-qPCR miRNA Taqman assay (UQmiR) for profiling miRNAs. In one embodiment, the present invention also involves use of computer programs (such as QmiR) for detection, quantification and/or profiling of miRNAs. In one embodiment, the RT-qPCR miRNA assay comprises one RT reaction with one universal RT primer, one universal reverse primer for the amplification reaction, miRNA-specific UQmiR forward primers, and one or more universal hydrolysis probes to sensitively detect all miRNAs (FIG. 5 and Table 2). The UQmiR forward primers only detect mature miRNA sequences, and do not amplify non mature miRNA sequences, such as genomic DNA, cDNAs of pre-miRNA, pri-miRNA and mRNA (FIG. 6).

In one embodiment, the present invention also comprises the use of a computer program, such as the QmiR computer program, to enhance specificity of the RT-qPCR miRNA Taqman assay (UQmiR) assay in the detection, quantification and/or profiling of miRNAs.

In a further embodiment, the present invention uses Surveyor nuclease that remove mis-matches caused by mis-priming to enhance specificity and/or single strand endonucleases such as Exonuclease I that remove single strand DNA such as excess primers. In another embodiment, the present invention uses uracil-DNA Glycosylase (UDG) and/or dUTP to enhance specificity.

Figure 13:
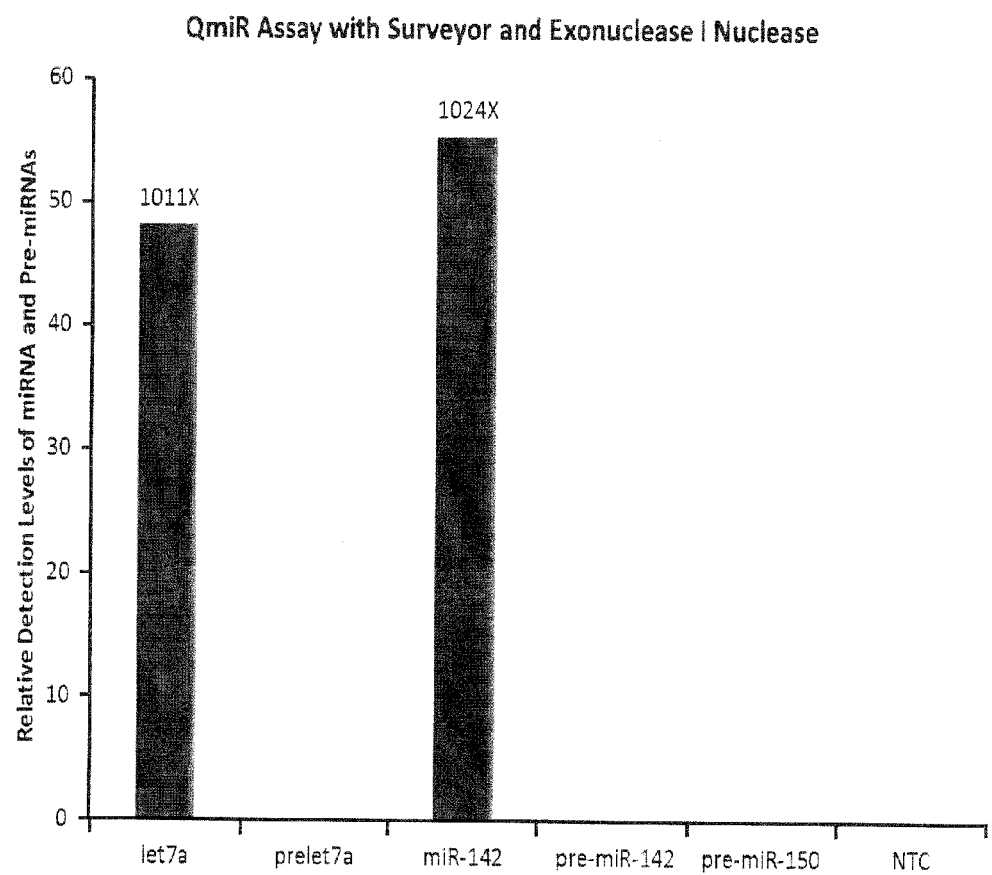
FIG. 13 shows discrimination of mature miRNA and pre-miRNA using the UQmiR miRNA qPCR assay with Surveyor nuclease, Exonuclease 1 nuclease and UQmiR primer that only has 3'-end extra sequence. UQmiR primers containing mature miRNA sequences were used to detect mature miRNA and pre-miRNA sequences. A total of 7.85E8 copies of synthetic Let-7a, miR-142, pre-Let-7a, pre-miR-142 and pre-miR-150 were added to RT reaction. The results show that UQmiR primer for detecting mature miRNA primers do not detect pre-miRNA well. The folds of discrimination are over one thousand times, which are shown above the each bar.

In one embodiment, UDG can be used to destroy the templates of any non-specific amplification when use dUTP-containing oligos as RT primers. FIGS. 13-15 describe various embodiments of using Surveyor nuclease, endonucleases, uracil-DNA Glycosylase (UDG) and/or dUTP for enhancing specificity and sensitivity.

Materials for miRNA Profiling

One aspect of the present invention provides materials for detecting, quantifying, and/or profiling miRNAs. In one embodiment, the materials comprise: a universal primer for reverse transcription of miRNAs, a universal reverse primer for PCR amplification reaction, and a universal probe. Also provided are reagents and kits for detecting, quantifying, and/or profiling miRNAs.

Design of Universal Primers for Reverse Transcription of miRNAs

In one aspect, the present invention provides a universal primer for reverse transcription of miRNAs. In some embodiments, the universal primer is an oligonucleotide sequence comprising: a $(dT)_n$ sequence flanked by a stem-looped universal adaptor sequence, wherein n is an integer ranges from 8 to 50, wherein the universal primer comprises at least two nucleotides adjacent to the 3'end of the $(dT)_n$ sequence, and the nucleotide immediately adjacent to the $(dT)_n$ sequence is not T, and wherein the universal adaptor sequence near the 5'end of the $(dT)_n$ sequence forms into a stem-loop structure by base-pairing. In one embodiment, the universal primer for reverse transcription is single-stranded DNA.

In some embodiments, n is 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, n can be an integer less than 10 or greater than 50.

In some embodiments, the universal primer comprises at least 2, 3, 4, 5, 6, 7, 8, 9, or 10 nucleotides are immediately adjacent to the 3'end of the $(dT)_n$ sequence.

In some embodiments, the adaptor sequence comprises 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 56, 57, 58, 59, or 60 nucleotides. In some embodiments, the adaptor sequence comprises more than 60 nucleotides. In some embodiments, each stem of the adaptor sequence located near the 5'end of the $(dT)_n$ sequence comprises 6, 7, 8, 9, 10, 11, 12, 13, 14, 15, 16, 17, 18, 19, 20, 21, 22, 23, 24, or 25 nucleotides. In one embodiment, the stems of the adaptor sequences base pair with each other (see FIGS. 1 and 5). In some embodiments, each stem of the adaptor sequence located near the 5'end of the $(dT)_n$ sequence comprises more than 25 nucleotides. In some embodiments, the loop of the adaptor sequence comprises 10, 11, 12, 13, 14, 15, 16, 17, 18, 19, 20, 21, 22, 23, 24, or 25 nucleotides. In certain embodiments, the loop of the adaptor sequence can comprise more than 25 nucleotides. In one embodiment, the loop of the adaptor comprises single-stranded nucleotides.

FIGS. 1 and 5 illustrate embodiments of the universal primer for reverse transcription of miRNAs. In a specific embodiment, the universal primer for reverse transcription of miRNAs comprises SEQ ID NO: 1. In some specific embodiments, the universal primer for reverse transcription of miRNAs comprises SEQ ID NO: 10 or SEQ ID NO: 13.

In some embodiments, the adaptor sequence (near the '5 end) of the universal primer for reverse transcription of miRNAs does not comprise a sequence that hybridizes, or base-pairs, with the target miRNA, wherein the sequence is at least 2, 3, 4, 5, 6, 7, 8, 9, 10, 11, 12, 13, 14, 15, 16, 17, 18, 20 nucleotides in length. In one embodiment, the universal primer for reverse-transcription is not target miRNA specific.

Design of Universal Reverse Primers for PCR Amplification Reaction

In one aspect, the present invention provides a universal reverse primer for PCR amplification reaction. In some embodiments, the universal reverse primer is an oligonucleotide comprising a sequence that is, or base-pairs with, at least part of the adaptor sequence (located near the 5'end of the $(dT)_n$ sequence) of the universal primer for reverse transcription. In some embodiments, the universal reverse primer is not target miRNA specific. In some embodiments, the universal reverse primer is single-stranded DNA.

In some embodiments, the universal reverse primer for PCR amplification comprises 8, 9, 10, 11, 12, 13, 14, 15, 16, 17, 18, 19, 20, 21, 22, 23, 24, or 25 nucleotides. In some embodiments, the universal reverse primer for PCR amplification comprises less than 8 or more than 25 nucleotides.

FIGS. 1 and 5 illustrate embodiments of the universal reverse primer for PCR amplification reaction. In a specific embodiment, the universal reverse primer for PCR amplification reaction comprises SEQ ID NO: 2.

In certain embodiments, the universal reverse primer for PCR amplification does not comprise a sequence that is, or base-pairs with, the target miRNA sequence. In one embodiment, the universal reverse primer for PCR amplification is not target miRNA specific.

In one embodiment, the universal reverse primer for PCR amplification comprises one or more dUTPs. In some embodiments, the universal reverse primer for PCR amplification reaction comprises SEQ ID NO: 11, SEQ ID NO: 14, or SEQ ID NO: 15.

Design of Forward Primers for PCR Amplification Reaction

In one aspect, the present invention provides a mature miRNA-specific forward primer for PCR amplification reaction. In one embodiment, the forward primer is miRNA-specific. In some embodiments, the forward primer comprises at least part of the target miRNA sequence. In some embodiments, the forward primer comprises the entire target miRNA sequence. In some embodiments, the forward primer is single-stranded DNA.

In some embodiments, the forward primer comprises at least 6, 7, 8, 9, 10, 11, 12, 13, 14, 15, 16, 17, 18, 19, 20, 21, 22, 23, 24, or 25 consecutive nucleotides of the target miRNA sequence. In one embodiment, the forward primer comprises one or more additional nucleotides (such as adenine molecules) attached to the 3' end of the target mature miRNA sequence. In some embodiments, 1, 2, 3, 4, 5, 6, 7, 8, or 9 nucleotides (such as adenine molecules) are attached to the 3' end of the target mature miRNA sequence. By attaching the additional nucleotides to the 3' end of the target miRNA sequence, the forward primer can detect the target miRNA sequence other than non mature miRNA sequences (e.g., genomic DNA and cDNAs of pre-miRNA, pri-miRNA) with higher specificity. As shown in FIG. 6, cDNAs of pre-miRNA, pri-miRNA and mRNA sequences and genomic DNA sequences do not extend at their 3'-end although they may anneal to the UQmiR forward primer comprising the additional nucleotides (such as adenine molecules).

In one embodiment, the forward primer comprises one or more additional nucleotides attached to the 5' end of the target mature miRNA sequence. In some embodiments, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 additional nucleotides are attached to the 5' end of the target mature miRNA sequence.

The number of nucleotides attached to the 3' and 5' ends of the forward primer can be adjusted to achieve the desired Tm of the forward primer. In some embodiments, Tm is about 60° C. to 75° C., 60° C. to 72° C., 65° C. to 72° C., 67° C. to 72° C., or 69° C. to 71° C. In some embodiments, Tm is about 65° C., 66° C., 67° C., 68° C., 69° C., 70° C., 71° C., 72° C., 73° C., 74° C., and/or 75° C. Preferably, Tin is about primer 70° C. In some embodiments, variation of Tin of the forward primer is within 0.5° C., 1° C., 1.5° C., 2° C., 2.5° C., 3° C., 3.5° C., 4° C., 4.5° C., 5° C., 5.5° C., 6° C., 6.5° C., 7° C., 8° C., 9° C., or 10° C. FIGS. 1, 5 and 6 illustrate embodiments of the forward primer for PCR amplification reaction.

Design of Universal Probes

In one aspect, the present invention provides a universal probe. The universal probes are useful for the detection and/or quantification of target miRNAs. In some embodiments, the universal probe is an oligonucleotide comprising a sequence that is, or base-pairs with, at least part of the adaptor sequence of the universal primer for reverse transcription. In some embodiments, the universal probe is single-stranded DNA.

In some embodiments, the universal probe further comprises a fluorophore, or other detectable moiety, attached at the ends of the oligonucleotide.

In certain embodiments, the universal probe in PCR amplification comprises 3, 4, 5, 6, 7, 8, 9, 10, 11, 12, 13, 14, 15, 16, 17, 18, 19, 20, 21, 22, 23, 24, or 25 nucleotides. In certain embodiments, the universal probe can comprise more than 25 nucleotides.

In some embodiments, a plurality of probes can be used for detection and/or quantification of target miRNAs. In some embodiments, the universal probe comprises one or more locked-nucleic acids (LNAs).

In a specific embodiment, the universal probe comprises a sequence that is, or base-pairs with, at least part of a stem-looped adaptor sequence near the 5'end of the (dT)n sequence of the adaptor sequence, wherein the probe comprises one or more locked nucleic acids.

FIGS. 1 and 5 illustrate embodiments of the universal probe. In a specific embodiment, the universal probe comprises SEQ ID NO: 3. In some specific embodiments, the universal probe comprise SEQ ID NO: 16, 17 or 18.

In certain embodiments, the universal probe does not comprise a sequence that is, or base-pairs with, the target miRNA sequence. In one embodiment, the universal probe is not target miRNA specific.

The detectable moiety is preferably a fluorophore. The fluorophores are preferably attached to the ends or near the ends of the oligonucleotide. When a probe of the invention hybridizes with a target nucleic acid sequence, the probe undergoes a conformational change to bring the fluorophores closer in proximity to each other. This change in distance causes a change in the photon absorption or emission of the fluorophores, creating a visual indication that the probe of the invention has bound a target sequence.

Fluorescent resonance energy transfer (FRET) or non-FRET interactions are used to detect the binding of the probe to its target sequence (e.g., PCR amplification products). FRET interactions (also known as non-radiative energy transfer; see Yaron et al., *Analytical Biochemistry* 95:228-235 (1979)) for quenching fluorescence signals requires spectral overlap between the donor and acceptor fluorophore moieties and the efficiency of quenching is directly proportional to the distance between the donor and acceptor moieties of the FRET pair. Extensive reviews of the FRET phenomenon are described in Clegg, R. M., *Methods Enzymol.*, 221: 353-388 (1992) and Selvin, P. R., *Methods Enzymol.*, 246: 300-334 (1995). In contrast, non-FRET interactions (also known as radiationless energy transfer; See: Yaron et al., *Analytical Biochemistry* 95:228-235 (1979)) requires short range interaction by "collision" or "contact" between the fluorophore moieties and therefore requires no spectral overlap between the donor and acceptor pair.

When the probe binds to the target sequence, the probe will undergo a conformational change causing the distance and/or angle between the fluorophore pairs to change. This change can then be detected because it will change the efficiency of resonance energy transfer between the fluorophore moieties after exposure of the probe to an excitation wave-length of light.

In one embodiment, fluorophores useful according to the present invention include, but are not limited to, FAM (6-carboxyfluorescein), CY5, CY3, BODIPY FL, and TEXAS RED. In a preferred embodiment, the fluorophore is FAM.

The universal primer, probe and adaptor sequences can be derived from universal probe and primer sequences known in the art, such as universal TaqMan® probe and primer sequences. For example, the design of the stem-loop universal adaptor sequence is described in (Chen, Ridzon, Broomer, Zhou, Lee, Nguyen, Barbisin, Xu, Mahuvakar, Andersen, Lao, Livak and Guegler. 2005. Real-time quantification of microRNAs by stem-loop RT-PCR. *Nucleic Acids Res* 33(20): e179).

The oligonucleotides of the present invention can encompass single and double-stranded RNA, single and double-stranded DNA and cDNA, nucleic acid analogs, aptamers, and the like. The terms "nucleic acid" and "oligonucleotide" are used interchangeably herein. Preferably, the oligonucleotide strands of the probe are single-stranded DNA.

"Hybridization" refers to a reaction in which one or more polynucleotides react to form a complex that is stabilized via hydrogen bonding between a particular purine and a particular pyrimidine in double-stranded nucleic acid molecules (DNA-DNA, DNA-RNA, or RNA-RNA). The major specific pairings are guanine with cytosine and adenine with thymine or uracil. Various degrees of stringency of hybridization can be employed. The more severe the conditions, the greater the complementarity that is required for duplex formation. Severity of conditions can be controlled by temperature, probe concentration, probe length, ionic strength, time, and the like.

Preferably, hybridization is conducted under high stringency conditions by techniques well known in the art, as described, for example, in Keller, G. H. & M. M. Manak, *DNA Probes*, and the companion volume *DNA Probes: Background, Applications, Procedures* (various editions, including 2$^{nd}$ Edition, Nature Publishing Group, 1993). Hybridization is also described extensively in the Molecular Cloning manuals published by Cold Spring Harbor Laboratory Press, including Sambrook & Russell, *Molecular Cloning: A Laboratory Manual* (2001). Each of these publications is incorporated herein by reference in its entirety.

A non-limiting example of high stringency conditions for hybridization is at least about 6×SSC and 1% SDS at 65° C., with a first wash for 10 minutes at about 42° C. with about 20% (v/v) formamide in 0.1×SSC, and with a subsequent wash with 0.2×SSC and 0.1% SDS at 65° C. A non-limiting example of hybridization conditions are conditions selected to be about 1, 2, 3, 4, 5, 6, 7, 8, 9, 10, 11, 12, 13, 14, 15, 16, 17, 18, 19, 20, 21, 22, 23, 24, or 25° C. lower than the thermal melting point ($T_m$) for the specific sequence in the particular solution. $T_m$ is the temperature (dependent upon ionic strength and pH) at which 50% of the target sequence hybridizes to a perfectly matched probe. $T_m$ typically increases with [Na$^+$] concentration because the sodium cations electrostatically shield the anionic phosphate groups of the nucleotides and minimize their repulsion. The washes employed may be for about 5, 10, 15, 20, 25, 30, or more minutes each, and may be of increasing stringency if desired.

Calculations for estimating $T_m$ are well-known in the art. For example, the melting temperature may be described by the following formula (Beltz, G. A., K. A. Jacobs, T. H. Eickbush, P. T. Cherbas, and F. C. Kafatos, *Methods of Enzymology*, R. Wu, L. Grossman and K. Moldave [eds.] Academic Press, New York 100:266-285, 1983).

$Tm=81.5°$ C.$+16.6$ Log [Na+]$+0.41$(% $G+C$)$-$
0.61(% formamide)$-600$/length of duplex in
base pairs.

A more accurate estimation of $T_m$ may be obtained using nearest-neighbor models. Breslauer, et al., *Proc. Natl. Acad. Sci. USA*, 83:3746-3750 (1986); SantaLucia, *Proc. Natl. Acad. Sci. USA*, 95: 1460-1465 (1998); Allawi & SantaLucia, *Biochemistry* 36:10581-94 (1997); Sugimoto et al., *Nucleic Acids Res.*, 24:4501-4505 (1996). $T_m$ may also be routinely measured by differential scanning calorimetry (Duguid et al., *Biophys J*, 71:3350-60, 1996) in a chosen solution, or by other methods known in the art, such as UV-monitored melting. As the stringency of the hybridization conditions is increased, higher degrees of homology are obtained.

Kits

The present invention also provides kits for detecting, quantifying, and/or profiling miRNA. In one embodiment, the kit comprises a universal primer for reverse transcription, a universal reverse primer for an amplification reaction (e.g., PCR), and/or a universal probe. Optionally, the kit can further comprise a forward primer sequence for an amplification reaction (e.g., PCR).

In a specific embodiment, the kit comprises SEQ ID NO:1 and/or SEQ ID NO:2. In another specific embodiment, the kit further comprises SEQ ID NO:3. In a further specific embodiment, the kit comprises one or more of SEQ ID NOs: 4-9. In a specific embodiment, the kit comprises one or more of SEQ ID NO:s 1-18.

Optionally, the kit may include any material useful for performing any step of the present invention. For instance, the kit may further comprise any material useful for reverse transcription of RNAs, and/or for profiling the target RNA. For instance, the kit may poly(A)polymerases, dNTPs, Adenosine-5'-triphosphates (ATP), DNA ligases (e.g., T4 DNA ligase), and Taq DNA polymerase.

The kit may also comprise, e.g., a buffering agent, a preservative, or a stabilizing agent. Each component of the kit is usually enclosed within an individual container and all of the various containers are within a single package along with instructions (e.g., printed instructions).

UQmiR qRT-PCR Assay

Another aspect of the present invention provides an assay for detecting, quantifying, and/or profiling miRNAs. Advantageously, the present invention can detect, quantify, and/or profile miRNAs in a sample of about 1 pg.

In one embodiment, the method for detecting, quantifying, and/or profiling a target miRNA comprises:

a) contacting a sample containing miRNAs with an effective amount of poly(A)polymerase molecules to yield 3' end-polyadenylated miRNA molecules, b) contacting the sample with an effective amount of a universal primer for reverse transcription and reverse transcriptases, and reverse transcribing the polyadenylated miRNA molecules to yield corresponding c-DNA molecules, and c) contacting the sample with an effective amount of a universal reverse primer and a target miRNA-specific forward primer, and amplifying the corresponding c-DNA molecules using an amplification reaction (e.g., PCR);

wherein the universal primer for reverse transcription is an oligonucleotide comprising: a $(dT)_n$ sequence flanked by a stem-looped universal adaptor sequence, wherein n is an integer ranges from 8 to 50, wherein the universal primer comprises at least two nucleotides adjacent to the 3'end of the $(dT)_n$ sequence, and the nucleotide immediately adjacent to the $(dT)_n$ sequence is not T, and wherein the universal adaptor sequence near the 5'end of the $(dT)_n$ sequence forms into a stem-loop structure by base-pairing, wherein the universal reverse primer for the amplification reaction is an oligonucleotide comprising a sequence that is, or base-pairs with, at least part of the adaptor sequence of the universal primer for reverse transcription.

In one embodiment, the forward primer comprises the target-miRNA sequence, one or more additional nucleotides (such as adenine molecules) attached to the 3' end of the target mature miRNA sequence. In some embodiments, 1, 2, 3, 4, 5, 6, 7, 8, or 9 nucleotides (such as adenine molecules) are attached to the 3' end of the target mature miRNA sequence. In one embodiment, the forward primer further comprises one or more additional nucleotides attached to the 5' end of the target mature miRNA sequence. In some embodiments, 1, 2, 3, 4, 5, 6, 7, 8, or 9 additional nucleotides are attached to the 5' end of the target mature miRNA sequence.

In a further embodiment, the assay comprises the steps of:
contacting the sample with an effective amount of a universal probe,
detecting and/or quantifying a level of amplified c-DNA molecules, and
determining the level of the target miRNA based on the c-DNA level.

In one embodiment, a plurality of probes can be used for detecting and/or quantifying a level of amplified c-DNA molecules. In some embodiments, 2, 3, 4, 5, 6, or 7 probes are used for detecting and/or quantifying a level of amplified c-DNA molecules. In one embodiment, the universal probe comprises a detectable moiety, for example, a fluorophore. In one embodiment, a plurality of detectable moieties (e.g., fluorophores) can be used.

In one embodiment, the amplification reaction (e.g., PCR) for amplifying cDNAs is quantitative real time polymerase chain reaction (qRT-PCR).

In one embodiment, the PCR reaction is performed once. In another embodiment, the reverse transcription reaction is performed once.

In one embodiment, the miRNA profiling assay of the present invention uses one universal primer for reverse transcription, one universal reverse primer in the amplification reaction (e.g., PCR), and/or one universal probe. In one embodiment, the miRNA profiling assay detects, quantifies, and/or profiles a plurality of target miRNAs.

In one embodiment, the threshold cycle (Ct) of the PCR amplification reaction ranges from 15 to 37. In preferred embodiments, the Ct value of the PCR amplification reaction ranges from 17 to 35, 20 to 30, 23 to 33, or 25 to 30. In certain embodiments, the Ct value is 15, 16, 17, 18, 19, 20, 21, 22, 23, 24, 25, 26, 27, 28, 29, 30, 31, 32, 33, 34, 35, 36, or 37. In one embodiment, the Ct value does not exceed 38.

Alternatively, the UQmiR qRT-PCR assay can be used for detecting, quantifying, and/or profiling nucleotide molecules, such as for example, siRNAs, oligonucleotides, polynucleotides, and/or mRNAs.

In one embodiment, samples containing miRNAs is a total RNA sample. In certain embodiments, the sample contains DNA, or has not been treated with DNases, or both. The samples can be derived from an organism, including mammals such as apes, chimpanzees, orangutans, humans, monkeys; and domesticated and/or laboratory animals such as dogs, cats, horses, cattle, pigs, sheep, goats, chickens, mice, rats, guinea pigs, and hamsters. The samples can be derived from, including but not limited to, a sample containing tissues, cells, and/or biological fluids isolated from a subject.

EXEMPLIFIED EMBODIMENTS

Embodiment 1

A method for detecting, quantifying, and/or profiling a target miRNA, comprising:
a) contacting a sample containing miRNAs with an effective amount of poly(A)polymerase molecules to yield 3' end-polyadenylated miRNA molecules,
b) contacting the sample with an effective amount of a universal primer for reverse transcription and reverse transcriptases, and reverse transcribing the polyadenylated miRNA molecules to yield corresponding c-DNA molecules; and
c) contacting the sample with an effective amount of a universal reverse primer and a target miRNA-specific forward primer, and amplifying the corresponding c-DNA molecules using an amplification reaction;
wherein the universal primer for reverse transcription is an oligonucleotide comprising: a $(dT)_n$ sequence flanked by a stem-looped universal adaptor sequence, wherein "n" is an integer ranging from 8 to 50, wherein the universal primer comprises at least two nucleotides adjacent to the 3'end of the $(dT)_n$ sequence, and the nucleotide immediately adjacent to the $(dT)_n$ sequence is not T, wherein the universal adaptor sequence near the 5'end of the $(dT)_n$ sequence forms into a stem-loop structure by base-pairing, and
wherein the universal reverse primer in the amplification reaction is an oligonucleotide comprising a sequence that is, or base-pairs with, at least part of the adaptor sequence near or toward the 5'end of the $(dT)_n$ sequence.

Embodiment 2

The method, according to embodiment 1, wherein the forward primer comprises the target miRNA sequence and three or more additional nucleotides attached to the 3' end of the target mature miRNA sequence.

Embodiment 3

The method, according to embodiment 1, wherein the additional nucleotides attached to the 3' end of the target mature miRNA sequence are adenine molecules.

Embodiment 4

The method, according to embodiment 2, wherein one or more additional nucleotides are attached to the 5' end of the target mature miRNA sequence.

Embodiment 5

The method, according to any of the preceding embodiments, wherein the amplification reaction for cDNA amplification is quantitative real time polymerase chain reaction (qRT-PCR).

Embodiment 6

The method, according to any one of embodiments 1-5, comprising:
contacting the sample with a sufficient amount of a universal probe,
detecting and/or quantifying a level of amplified c-DNA molecules, and
determining the level of the target miRNA based on the c-DNA level;
wherein the universal probe comprises a sequence that is, or base-pairs with, at least part of the adaptor sequence near the 5'end of the $(dT)_n$ sequence.

Embodiment 7

The method, according to embodiment 6, wherein the universal probe comprises locked nucleic acid (LNA) molecules.

Embodiment 8

The method, according to embodiment 6 or 7, wherein the universal probe includes a detectable moiety.

Embodiment 9

The method, according to embodiment 8, wherein the detectable moiety is a fluorophore selected from FAM, CY5, CY3, BODIPY FL, TEXAS RED, or any combination of two or more of the foregoing.

Embodiment 10

The method, according to any one of embodiments 6-9, wherein at least two universal probes are used.

Embodiment 11

The method, according to any one of the preceding embodiments, wherein the amplification reaction for amplification of cDNA molecules is performed once.

Embodiment 12

The method, according to any one of the preceding embodiments, wherein the threshold cycle (Ct) of the amplification reaction for amplification cDNA molecules ranges from 17 to 35.

Embodiment 13

The method, according to any one of the preceding embodiments, wherein the sample is a total RNA sample.

Embodiment 14

The method, according to any one of the preceding embodiments, wherein the method is capable of detecting, quantifying and/or profiling microRNA in a total RNA sample of about 1 pg.

Embodiment 15

The method, according to any one of the preceding embodiments, wherein the universal reverse primer comprises dUTP.

Embodiment 16

The method, according to embodiment 15, further comprising adding uracil-DNA Glycosylase molecules to the amplification reaction mixture.

Embodiment 17

The method, according to any one of the preceding embodiments, comprising adding nuclease molecules to the reaction mixture.

Embodiment 18

A universal primer for detecting, quantifying and/or profiling miRNA, wherein the universal primer is a primer for reverse transcription of miRNAs, wherein the universal primer is an oligonucleotide comprising: a $(dT)_n$ sequence flanked by a stem-looped universal adaptor sequence, wherein "n" is an integer ranging from 8 to 50, wherein the universal primer comprises at least two nucleotides adjacent to the 3'end of the $(dT)_n$ sequence, and the nucleotide immediately adjacent to the $(dT)_n$ sequence is not T, and wherein the universal adaptor sequence near the 5'end of the $(dT)_n$ sequence forms into a stem-loop structure by base-pairing.

Embodiment 19

A universal primer for detecting, quantifying and/or profiling miRNA, wherein the universal primer is a reverse primer for an amplification reaction, wherein the universal primer is an oligonucleotide comprising a sequence that is, or base-pairs with, at least part of the adaptor sequence near the 5'end of the $(dT)_n$ sequence according to embodiment 18.

Embodiment 20

The universal reverse primer for an amplification reaction according to embodiment 19, wherein the universal reverse primer comprises dUTP.

Embodiment 21

A universal probe for detecting, quantifying and/or profiling miRNA, wherein the universal probe comprises a sequence that is, or base-pairs with, at least part of the adaptor sequence near the 5'end of the $(dT)_n$ sequence of embodiment 18.

Embodiment 22

The universal probe according to embodiment 21, further comprising a detectable moiety.

Embodiment 23

The universal probe according to embodiment 21 or 22, wherein the detectable moiety comprises a fluorophore.

Embodiment 24

The universal probe according to any one of embodiments 21-23, comprising locked nucleic acid (LNA) molecules.

Embodiment 25

A kit for detecting, quantifying and/or profiling a level of expression of miRNA, comprising a universal primer for reverse transcription according to embodiment 18; and a universal reverse primer for an amplification reaction according to embodiment 19 or 20.

Embodiment 26

The kit according to embodiment 25, further comprising a universal probe of any one of embodiments 21-24.

Materials and Methods

Table 1 illustrates oligonucleotide sequences useful according to the present invention.

TABLE 1

| Name | Sequence (5' to 3') |
| --- | --- |
| RTUloop | TGGCTAGTTAAGCTCACCAGCTCGGTACCAAGCTTAACTAGC CA(T)25N*N** (SEQ ID NO: 1) |

TABLE 1-continued

| Name | Sequence (5' to 3') |
|---|---|
| QRTU | TGGCTAGTTAAGCTCACCAGCTCG (SEQ ID NO: 2) |
| miRU probe | FAM/TGGCTAGTTAAGCTTGGTACCGAGCT/IAB1k_FQ (SEQ ID NO: 3) |
| Let-7a | TGAGGTAGTAGGTTGTATAGTT (SEQ ID NO: 4) |
| miR-21 | TAGCTTATCAGACTGATGTTGA (SEQ ID NO: 5) |
| miR-142 | TGTAGTGTTTCCTACTTTATGGA (SEQ ID NO: 6) |
| miR-150 | TCTCCCAACCCTTGTACCAGTG (SEQ ID NO: 7) |
| miR-494 | TGAAACATACACGGGAAACCTCTT (SEQ ID NO: 8) |
| mmu-miR-690 | AAAGGCTAGGCTCACAACCAAA (SEQ ID NO: 9) |

N* = A, G, or C; N** = A, G, C, or T.

ABBREVIATIONS: miRNAs: MicroRNAs; UPR: a universal probe and RT primer; qRT-PCR: quantitative real-time reverse transcription PCR; QRTU: universe reverse primer; RTUloop: universal RT primer; FAM: 6-carboxyfluorescein; CT: threshold cycle.

TABLE 2

| Name | Sequence (5' to 3') |
|---|---|
| Longshort RT primer | CCATCAATCGTGTGTCTCTATGGATGCTGTCACAACGACATGTCAGCC TCTGACTCCAGGATCTGTAGACGCTAGCTGACATGTCGTTGTGACAGC ATCCATAGAGACACACGATTGATGGTTTTTTTTTTTTTTTTTTTTTTTT N*N** (SEQ ID NO: 10) |
| NewURP | GCCTCTGACTCCAGGATCTGTAGAC (SEQ ID NO: 11) |
| Ublocker | CGACAUGUCAGCUAGGUCGUttCGGUttCACUAUCGCUACGCACAG (SEQ ID NO: 12) |
| LUTVN RT primer | CUGUGCGUAGCGAUAGUGAAACCGAAACGACCUAGCUGACAUGUCG TTTTTTTTN*N** (SEQ ID NO: 13) |
| 384URP | CTGTGCGTAGCGATAGTGAAACCGAAAC (SEQ ID NO: 14) |
| URP | CGCTGTACTCCAGGATCTGTAGACG (SEQ ID NO: 15) |
| LNADLP1 | [6FAM]ACC[A][T][C]A[A][T][C]G[T]G[T]G[BHQ1]** (SEQ ID NO: 16) |
| LNADLP2 | [6FAM]CT[A][T][G]G[A]T[G]C[T]G[T][C]A[BHQ1]** (SEQ ID NO: 17) |
| LNADLP3 | [6FAM]C[G]A[C]AT[G][T][C]A[G][C][T]AG[BHQ1]** (SEQ ID NO: 18) |

N* = A, G, or C; N = A, G, C, or T.  The bases in parenthesis are special bases called LNAs (locked nucleic acids).

EXAMPLES

Following are examples which illustrate procedures for practicing the invention. These examples should not be construed as limiting. All percentages are by weight and all solvent mixture proportions are by volume unless otherwise noted.

Example 1

The Universal Probe—RT Primer (UPR) MicroRNA Real-Time qRT-PCR Assay

FIG. 1 illustrates one embodiment of the universal probe-RT primer (UPR) real-time qRT-PCR assay for profiling microRNAs. The assay comprises a three-step process. First, total RNA is polyadenylated using poly(A)polymerase molecules. The polyadenylated miRNAs are reversely transcribed into cDNAs using a universal RT primer (RTUloop) with 25-T poly (T) at 3' end. Finally, the RT product is amplified by qPCR using the mature target miRNA sequence as the forward primer and a universal reverse primer (QRTU). The amplification products can be detected or quantified using a miRU fluorescent probe, such as for example, a 26-nucleotide universal TaqMan® probe.

MiRNA Sequences and Primers

About 800 human and mouse miRNA genes are selected from the Sanger Institute miRBase Sequence Database. miRNA expression profiling was performed and analyzed using the dot-blot array as previously described (Wang and Cheng. 2008. A simple method for profiling miRNA expression, Methods Mol Biol 414: 183-90), 96 miRNAs were selected for miRNA QPCR array assay from the dot blot array results.

The miRNA universal TaqMan® probe was designed by PrimerQuest (Table 1) based on sequences described in Ro et al. The stem-loop adaptor contained in the RT primers were designed according to Chen et al. (Chen, Ridzon, Broomer, Zhou, Lee, Nguyen, Barbisin, Xu, Mahuvakar, Andersen, Lao, Livak and Guegler. 2005. Real-time quantification of microRNAs by stem-loop RT-PCR. Nucleic Acids Res 33(20): e179). All DNA oligonucleotides were synthesized by IDT.

Preparation of RNA and cDNA

Total RNA was isolated from spleens of 4-week-old Balb/C mice using Trizol (Invitrogen) following the manufacturer's protocol. Total RNAs (1 µg) was incubated with poly(A)polymerase (USB) molecules, thereby generating polyadenylated microRNAs at the '3 end. The polyadenylated RNAs (20 µl) reverse transcribed using 2 µM RTUloop primer, 0.25 mM each of dNTPs, 100 units Smartscribe reverse transcriptase, 1× reverse transcriptase buffer, and 10 mM DTT (Clontech Laboratories). The reactions were incubated at 42° C. for 90 minutes, and then at 95° C. for 5 minutes, to inactivate reverse transcriptase molecules and to degrade RNAs. All reverse transcriptase reactions included no-template and minus-RT as controls.

Real-Time PCR

1 µl 10-time serially diluted reverse transcription reactions were used for real-time PCR, using the target miRNA as the forward primer and QRTU as the universal reverse primer. All the reactions were run on the ABI 7900HT System (Applied Biosystems). Real-time PCRs were carried out in a 20 µl reaction in triplicate.

Amplification curves were generated with an initial denaturing step at 95° C. for 30 seconds, followed by 40 cycles at 95° C. for 5 seconds, and at 60° C. for 30 seconds. Dissociation curves were generated using the following programs: PCR products were denatured at 95° C. for 15 seconds, cooled to 60° C. for 15 seconds, and finally at 95° C. for 15 seconds.

All QPCRs were carried out using Premix Ex Taq™ or SYBR Premix II Ex Taq (Perfect Real Time) (Clontech Laboratories). SYBR Green 1 and TaqMan® PCR products were visualized on 2% agarose gels by Grow-Green staining (eEnzyme).

Example 2

Reproducibility of the UPR microRNA qRT-PCR Assay

Figure 2A:
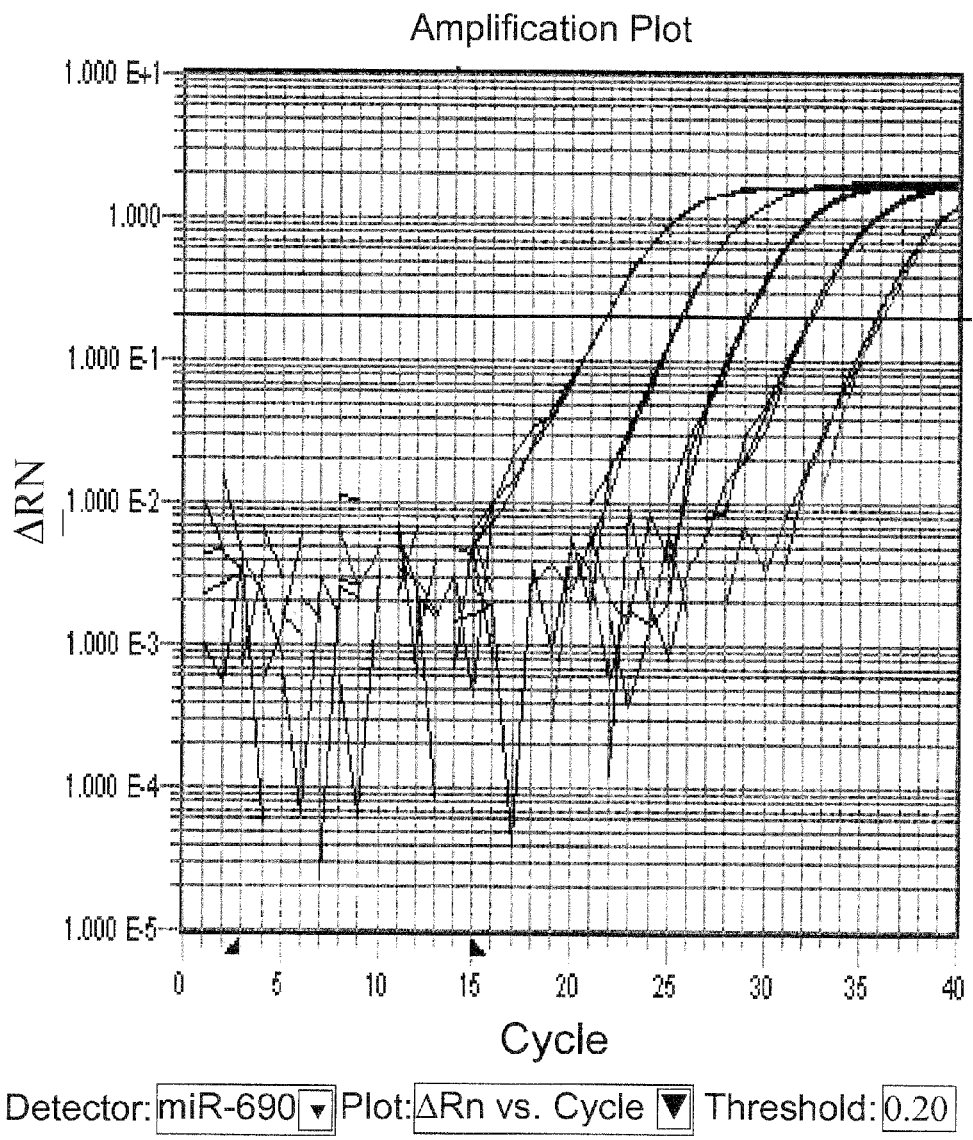
FIG. 2 shows characteristics of the universal probe and RT primer (UPR) miRNA real-time quantitative PCR (qRT-PCR) assay. (A) Amplification curve plot of miR-690 UQmiR qRT-PCR assay. (B) Relative standard curve plot of miR-690 UQmiR qRT-PCR assay calculated over 10 serial dilutions. Average $C_T$ values (y-axis) are plotted against the logarithm of the input amount of RNA (x-axis) added to each sample. Standard curve of the slope was −3.4 and correlation coefficient was 0.9995. (C) Correlation of total RNA input to the threshold of cycle (CT) values in four miRNA assays. Mouse spleen total RNA input ranged from 10 ng to 0.1 pg per RT reaction. (D) Amplification curve plot of 96 miRNA amplicons in a UQmiR qRT-PCR assay. The experiments were conducted in triplicate. During QPCR, a forward primer specific to each target miRNA and a universal reverse primer (QRTU) were used.
Figure 2B:
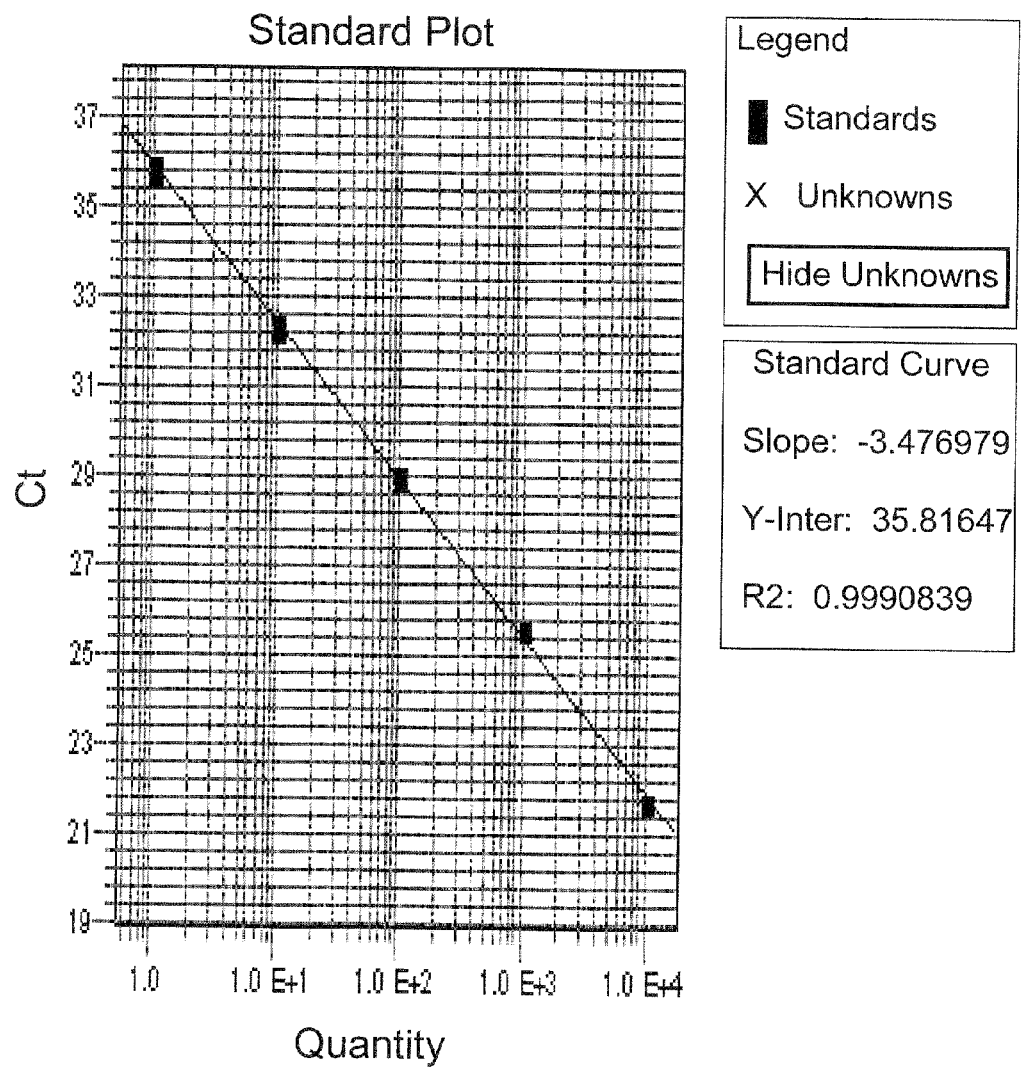
Figure 2C:
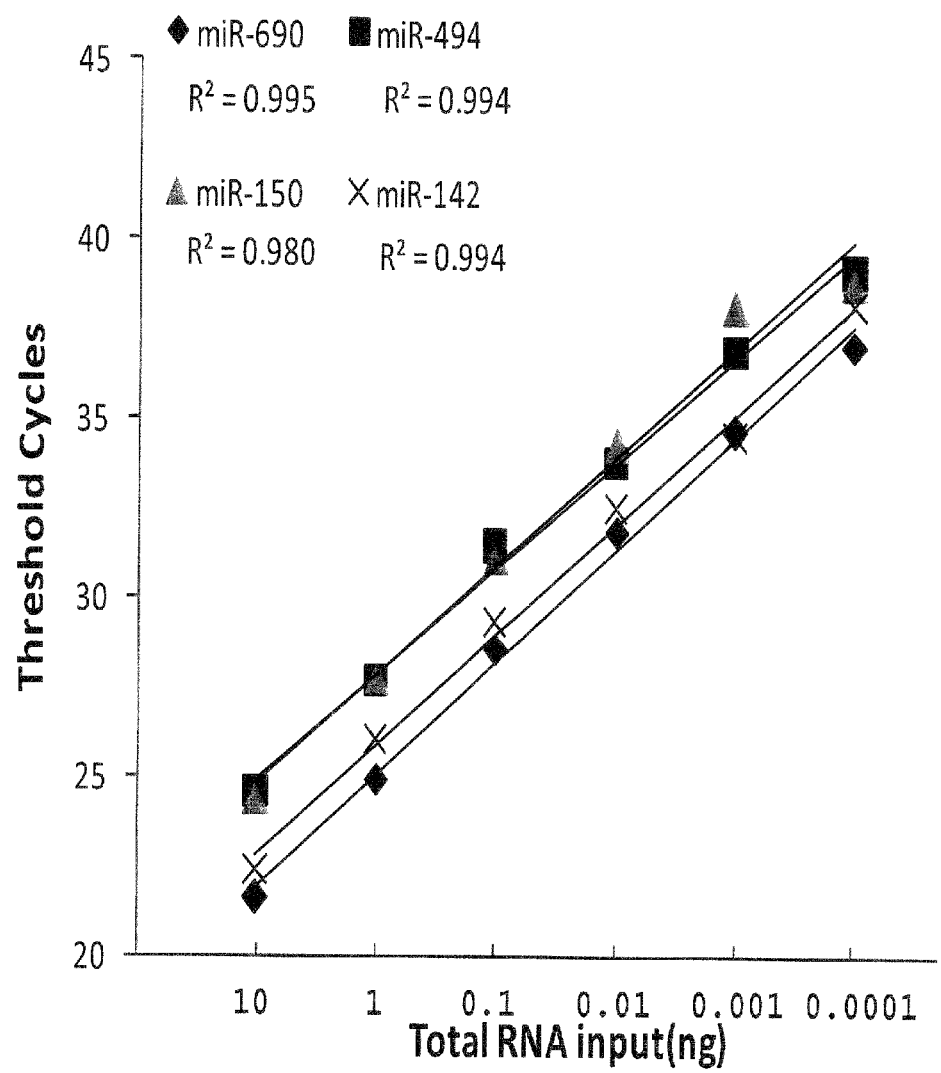

The amplification efficiency is critical a reproducible qRT-PCR assay. To examine, the reproducibility of the UPR miRNA qRT-PCR assay, amplification efficiency was calculated using the relative standard curve method (FIGS. 2B&C). Briefly, qRT-PCR cDNA templates of miRNAs were prepared by 10-time serial dilution, which is equivalent to 10, 1, 0.1, 0.01 and 0.001 ng of total RNA, respectively. Each sample was run in triplicate.

The standard curves were generated using the Prism HT7900 system. The correlation coefficient (R2) values were greater than 0.99 (except for that of miR-150, which is 0.98), indicating excellent linear reliability between RNA concentration and the $C_r$ value of reverse transcription real-time PCR reaction for each miRNA.

PCR efficiency was calculated by the formula $E=-1+10^{-1/slop}$. FIGS. 2A&B show the amplification curve plot and standard curve plot of the miR-690 qRT-PCR. The PCR efficiency is 0.94 for miR-690 and 1.1 for miR-142 and miR-150 (efficiencies between 0.90 and 1.10 are typically acceptable).

Figure 2D:
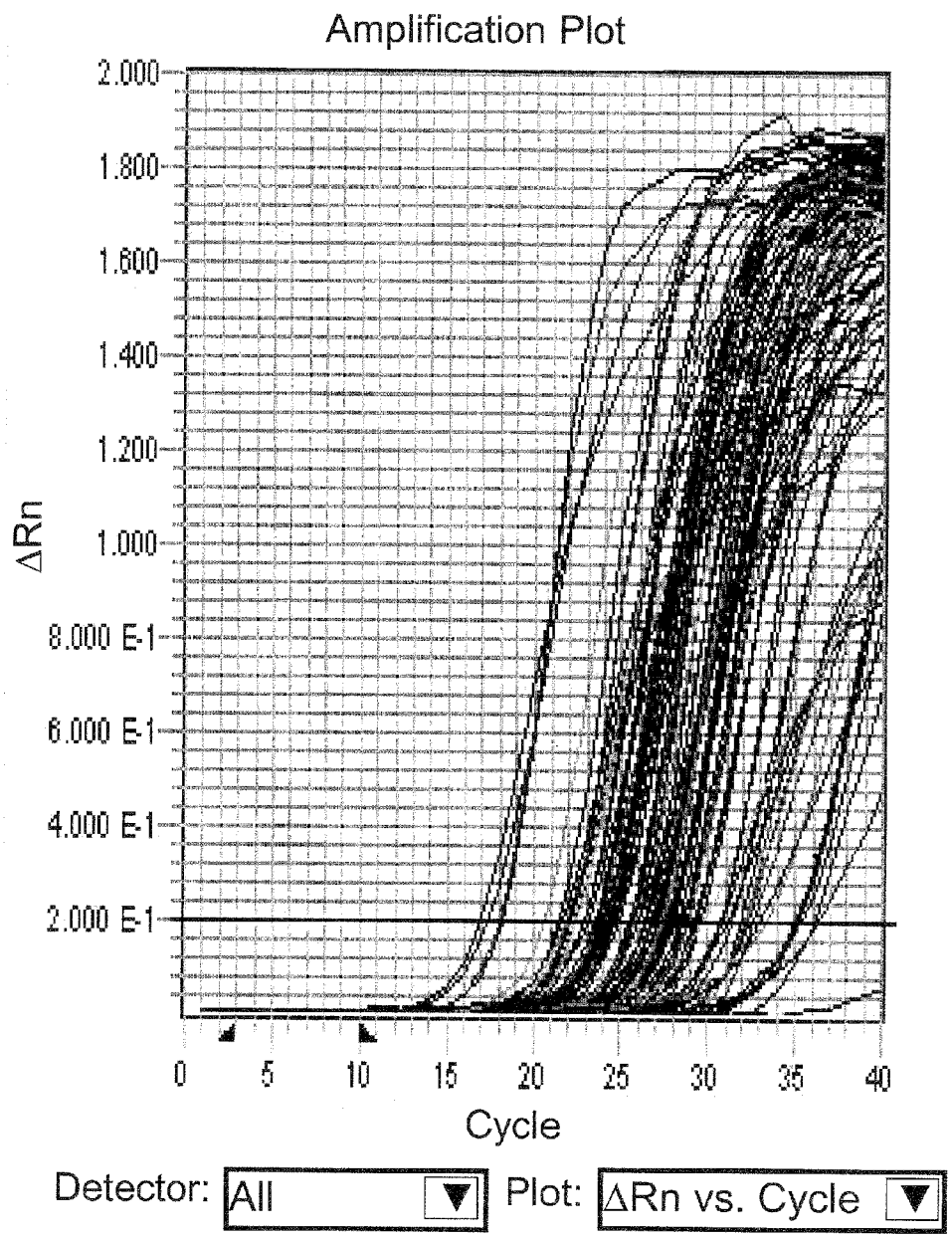

Amplification curves correlated to the concentration of RNA template and spanned five orders of magnitude (FIGS. 2A&B). The CT values from the amplification curves for the 96 miRNA QPCR array range from 17 to 35, equivalent to five orders of magnitude (FIG. 2D).

Example 3

Specificity of the UPR microRNA qRT-PCR Assay

Without the use of DNases, no RNA isolation method can consistently produce RNA free from genomic DNA contamination. This Example tests whether residual genomic DNA contamination may cause non-specificity of the UPR miRNA qRT-PCR assay.

Briefly, mouse tail genomic DNA, isolated by the DNeasy Blood & Tissue Kit (QiaGen), was used as the template in the UPR miRNA qRT-PCR assay. Mouse tail genomic DNA was added during the polyadenylation reaction (0.3 µg genomic DNA used), or QPCR reactions as templates (1 µg genomic DNA used).

Figure 3A:
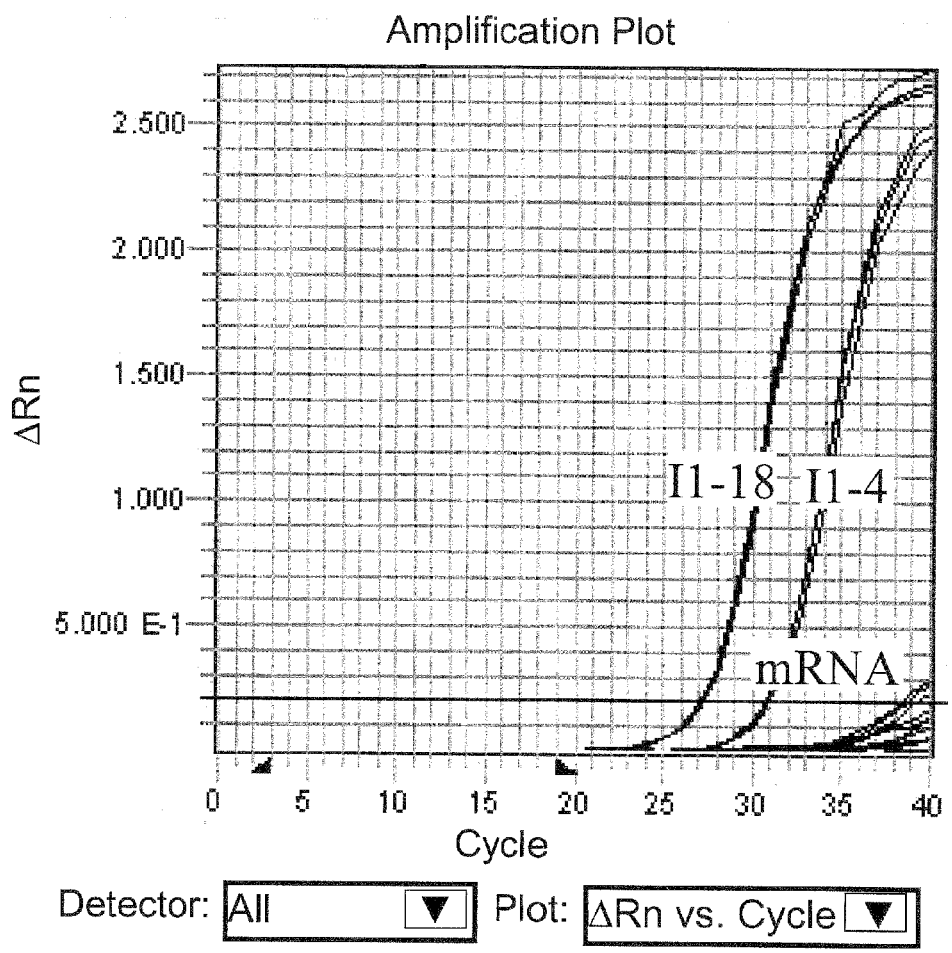
FIG. 3 shows that the UPR Q-RT-PCR assay is miRNA-specific. (A) Amplification curve plot of the UPR miRNA qRT-PCR assay, using total RNA as the template for reverse transcription without the step of polyadenylation (mRNA). When mRNAs are used as templates for amplification of let-7, miR-21, miR-142, miR-150 and miR-494, the cycle threshold values (Cts) of qRT-PCRs are greater than 38. NTCs (nontemplate controls) did not produce any detectable signals. The 11-4 and 11-18 amplifications of the cDNA molecules serve as positive controls of the RT reaction. (B) Amplification curve plot of the UPR miRNA qRT-PCR assay for let-7, miR-21, miR-142, miR-150, miR-494 and miR-690. Mouse tail genomic DNA (DNA) and transcribed spleen total RNA (miRNA, served as positive controls) were subjected to polyadenylation and reverse transcription reactions. There are no detectable signals for the DNA template. (C) Amplification curve plot of UPR miRNA qRT-PCR assay using mouse tail genomic DNA as the template of the 96 miRNA qPCR array. (D) Agarose gel image of the 12 miRNA reactions from the 96-miRNA qPCR array assay. After 40 cycles, products were electrophoresed on 2% agarose gels. A 1 kb DNA marker (Invitrogen) was loaded on the left side of the gel.
Figure 3B:
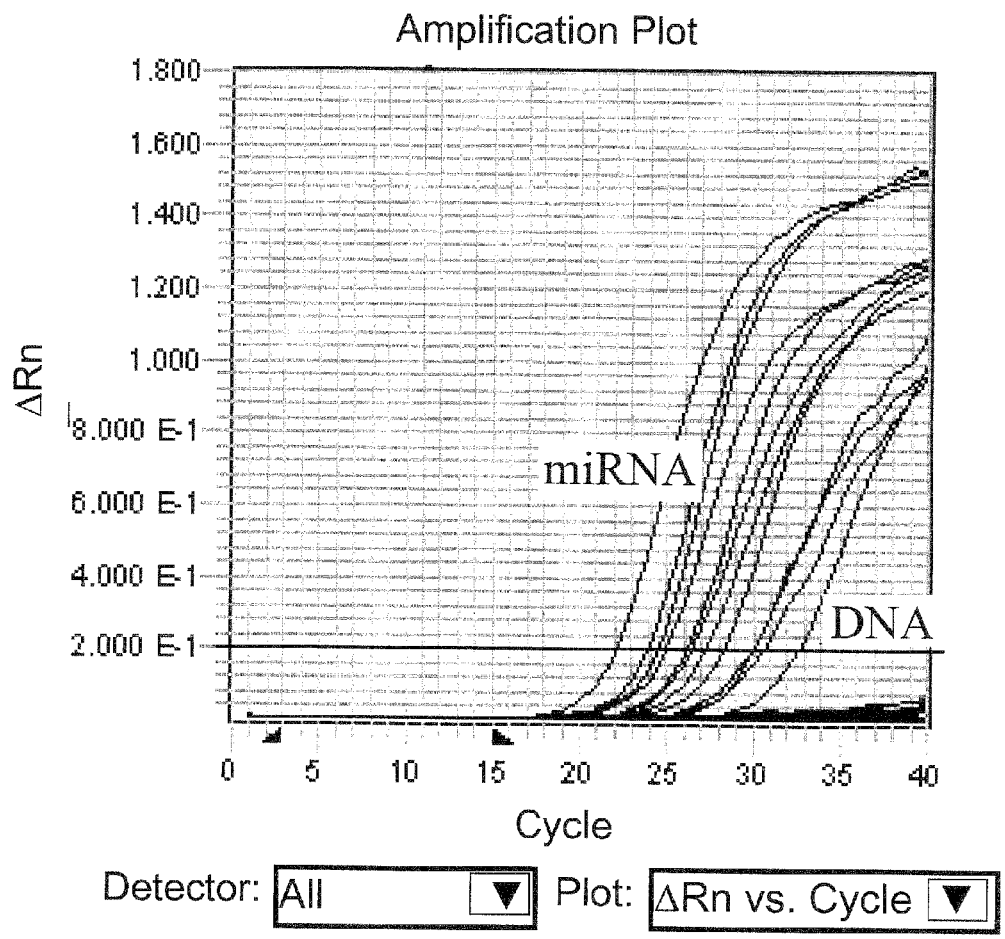
Figure 3C:
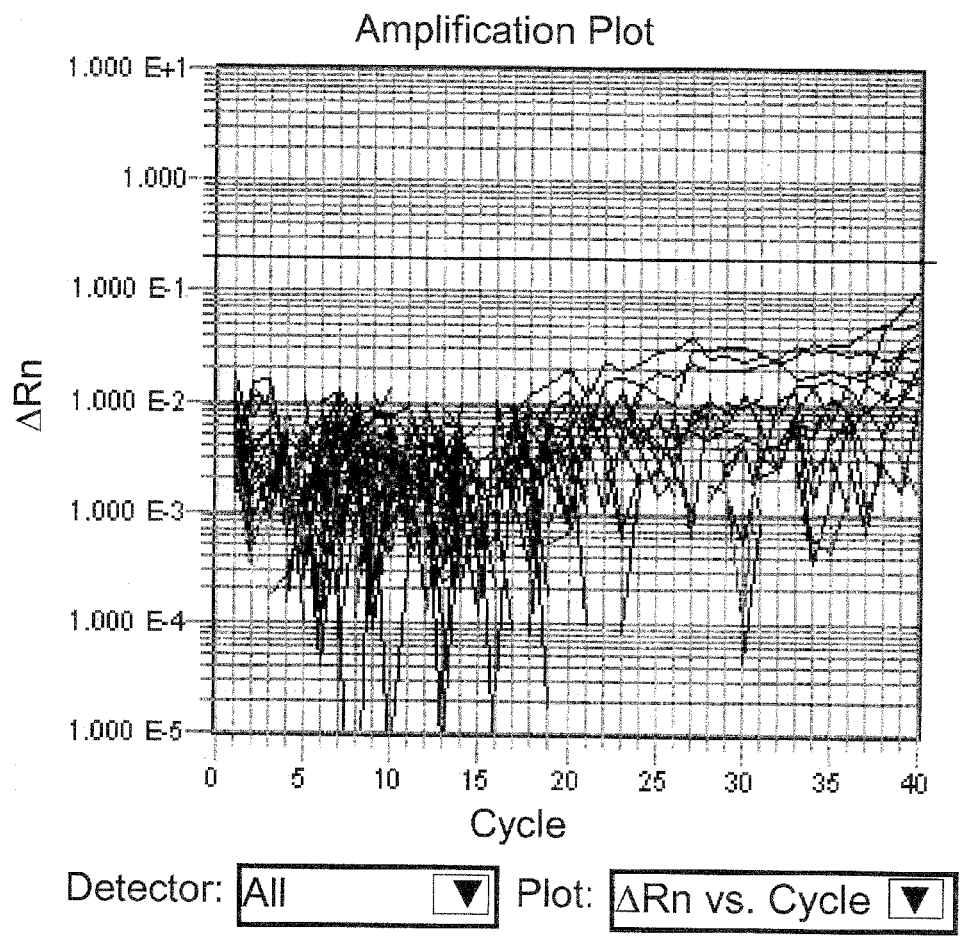
Figure 3D:
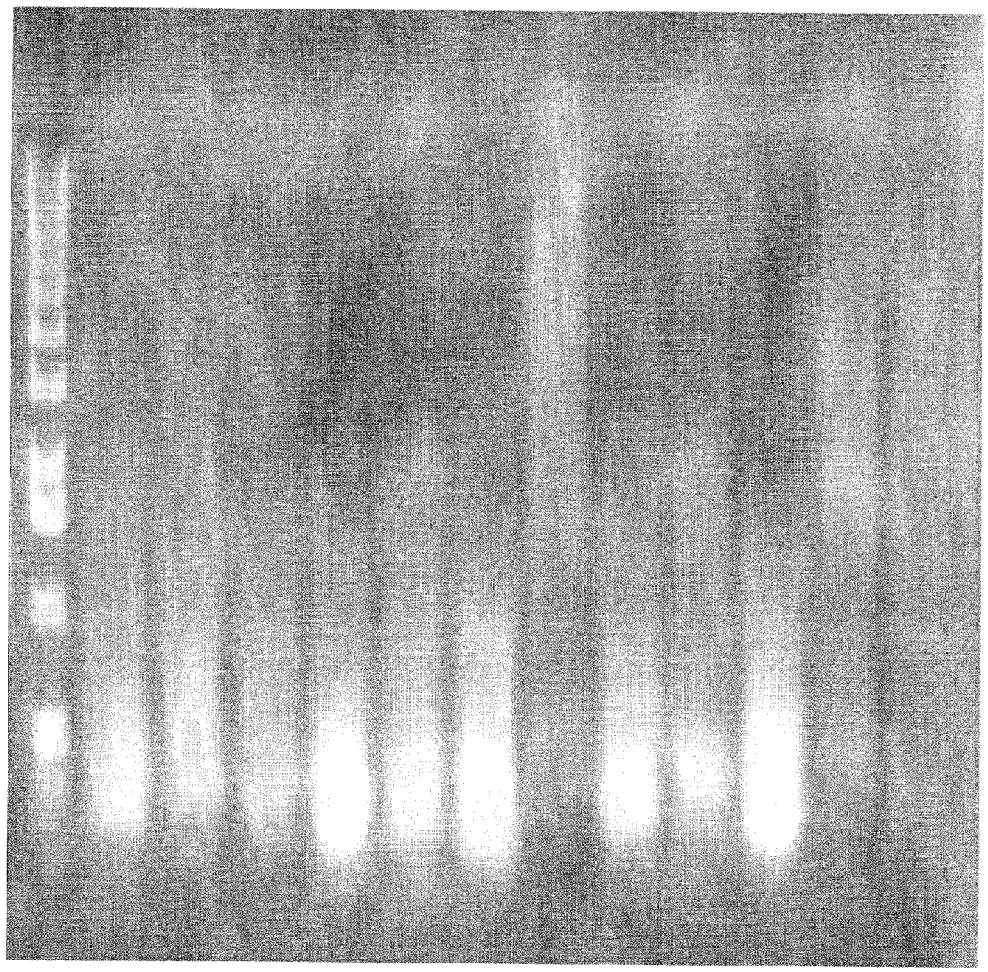

The results show no detectable signals in the UPR miRNA QPCR assay, when using genomic DNA either as a sham control for the total RNA (FIG. 3B), or as the direct template of QPCR (FIG. 3CC). The agarose gel electrophoresis shows nonspecific amplification (FIG. 3D), which may be detected by SYBR Green. The amount of the genomic DNA used in this Example far exceeds residual. DNA that may be present in total RNA preparation. This indicates that the accuracy of the UPR miRNA qRT-PCR assay will not be affected by genomic DNA contamination in total RNA preparation.

Total RNA was also used as the template of UPR miRNA qRT-PCR assay without the polyadenylation step. This investigates whether mRNAs, the major component of total RNA, will produce significant non-specific signals in the assay. When polyadenylated mRNA is used as the template of the qRT-PCR assay, the CTs (threshold cycle) of qRT-PCR assays are greater than 38 (FIG. 3A). CT values greater than 35 approaches the sensitivity limits of the real-time PCR detection system of miRNAs. This suggests that the contribution of the background signals from mRNA in this assay is negligible.

Example 4

Detection of Non-Specific Amplification by microRNA SYBR Green QPCR Array

SYBR Green is a fluorescent dye. It non-specifically intercalates into double-stranded DNA and detects double-stranded DNA.

Figure 4A:
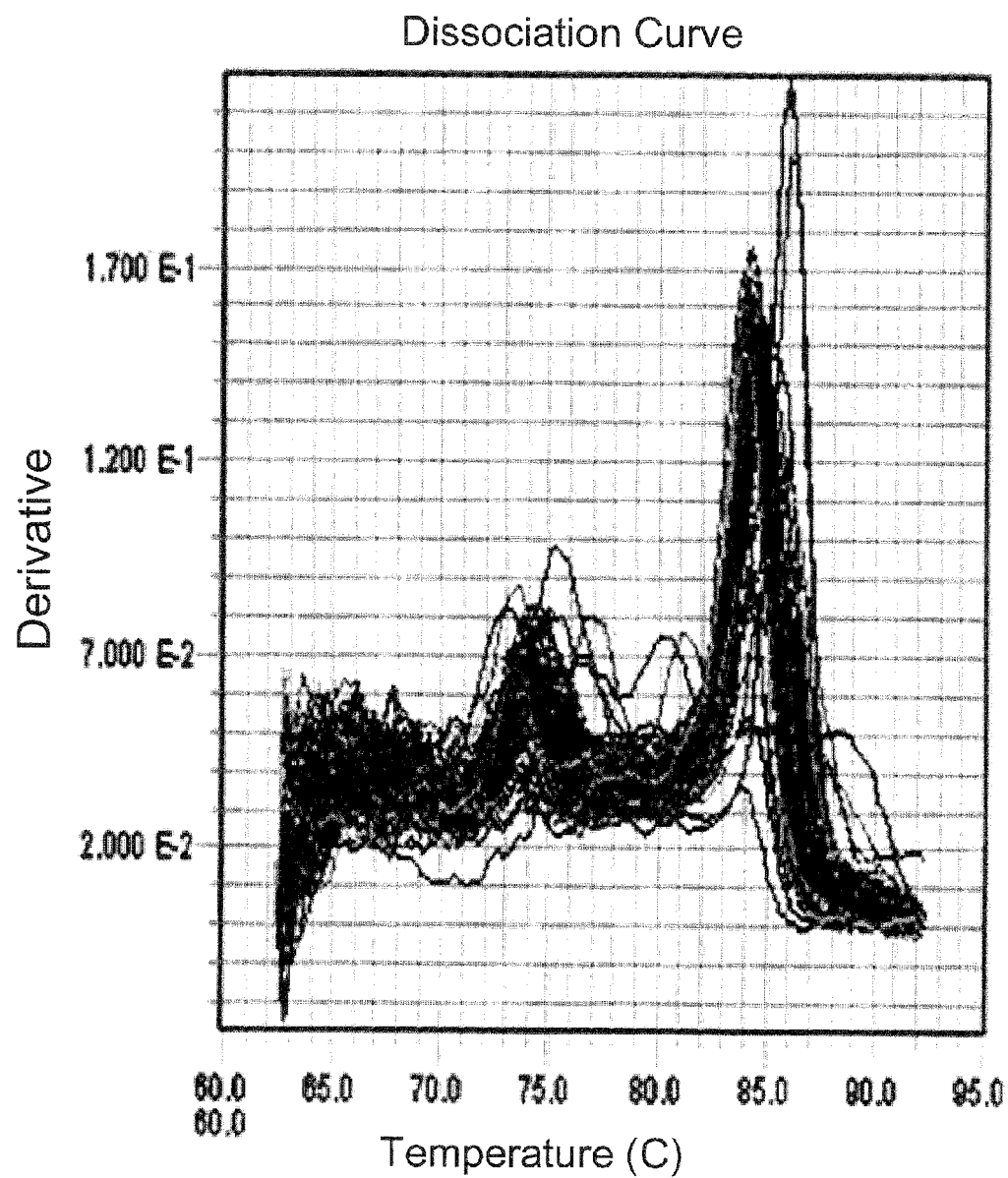
FIG. 4 shows characteristics of the SYBR Green real-time quantitative PCR (qRT-PCR) assay for 96 miRNAs. The SYBR Green Q-PCRs were performed using SYBR Green. For each miRNA, a forward primer specific to the target miRNA and a universal reverse primer were used for qPCR amplification. (A) Dissociation curves of all 96 miRNA amplicons amplified using miRNA cDNAs prepared from mouse spleens. (B) Amplification curve plot of 96 miRNA amplicons of the SYBR Green Q-PCR assay. The experiments were conducted in triplicate.
Figure 4B:
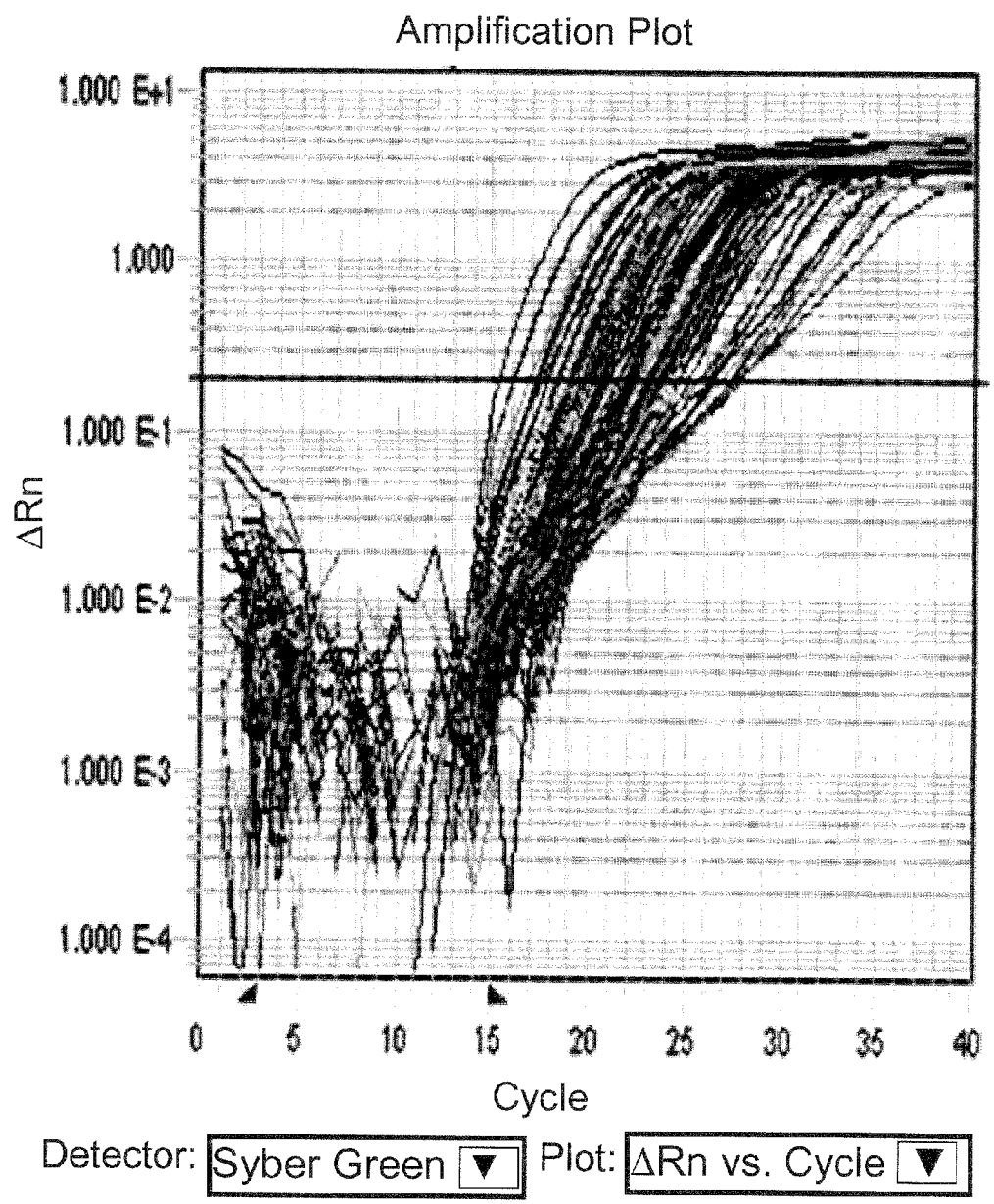

FIG. 4 shows detection of non-specific amplification by 96-miRNA qRT-PCR array using SYBR Green. The dissociation curves (FIG. 4A) show that most miRNA qRT-PCRs produced a small peak and a major peak. The small peak represents non-specific amplification, while the major peak represents amplification of the desired PCR products. The log amplification curve plot (FIG. 4B) shows that there are non-exponent amplifications for low abundant miRNAs. The results suggest that the SYBR Green assay may over-detect miRNAs, which is present in low amounts.

Example 5

Use of Multiple Hydrolysis Locked-Nucleic Acid (LNA) Probes Improves Sensitivity of UQmiR RT-QPCR Assay In this Example, multiple hydrolysis locked-nucleic Acid (LNA) probes are used to sensitively detect amplicons of the amplification reaction (FIG. 5). Use of a plurality of probes significantly enhances sensitivity for miRNA profiling and the increase in sensitivity equals to the number of probes used minus 1. This technique is especially useful for detecting low copy of miRNAs and/or detecting miRNAs in small samples. For example, miRNAs present in samples obtained from laser capture microdissection microscopy (LCMM) or a single cell can be detected using the present probe design. Such low copy of miRNAs cannot be detected using the commercially-available miRNA detection methods.

Figure 7:
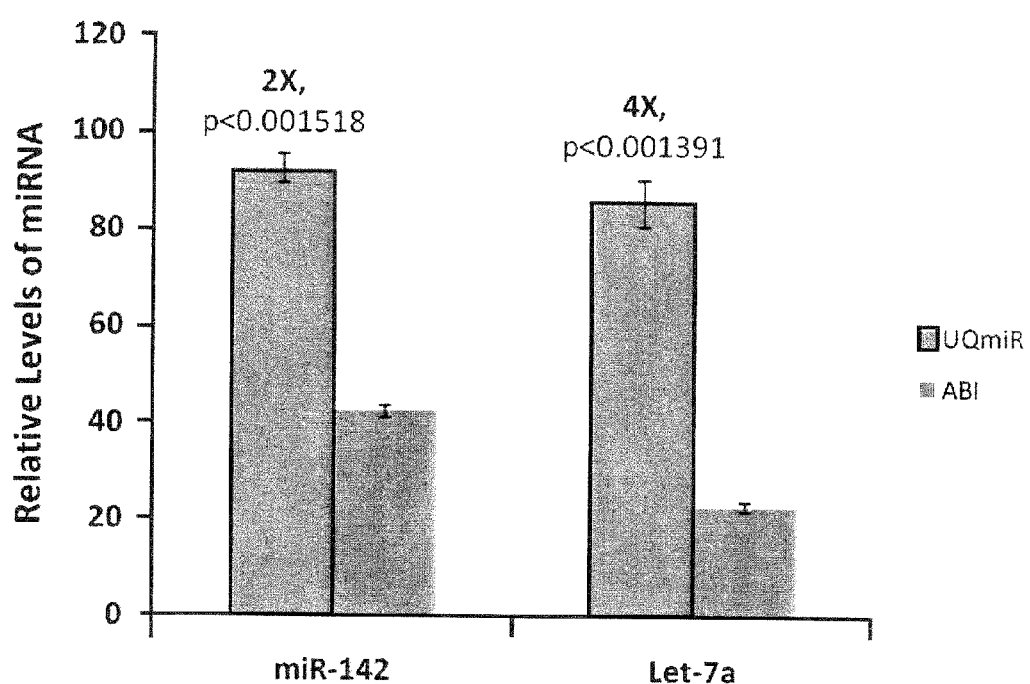
FIG. 7 compares the sensitivity of the RT-qPCR reaction between the UQmiR assay of the present invention and the commercially-available miRNA RT-qPCR Taqman assay (Applied Biosystems (ABI)). Same amounts of synthetic miR-142 and Let-7a mature miRNAs were used for both miRNA RT-qPCR assays following the manufacturer's instruction. The results show that the UQmiR assay of the present invention is at least two times more sensitive than the commercially-available Taqman assay.

FIG. 7 shows that the UQmiR assay of the present invention is more sensitive than the Taqman RT-qPCR assay, which is the most sensitive and specific miRNA assay currently available.

Example 6

Use of UQmiR Forward Primer Enhances Specificity of UQmiR RT-QPCR Assay

This Example illustrates one embodiment of the forward primer (UQmiRprimer) useful for the amplification reaction of the present miRNA assay. In one embodiment, the forward primer comprises the target mature miRNA sequence and additional nucleotides attached to the 5' and 3' ends of the mature miRNA sequences.

As shown in FIG. 6, by attaching additional sequences at the 5' and 3'-ends of the mature miRNA sequences, the UQmiR primers specifically bind to the cDNAs of mature miRNAs and extension occurs at both ends. The forward primer does not anneal to non mature miRNA sequences such as genomic DNA, cDNAs of pre-miRNA, pri-miRNA and mRNA that comprise the mature miRNA sequence; therefore, no extension occurs in non mature miRNA sequences.

Figures 8A, 8B:
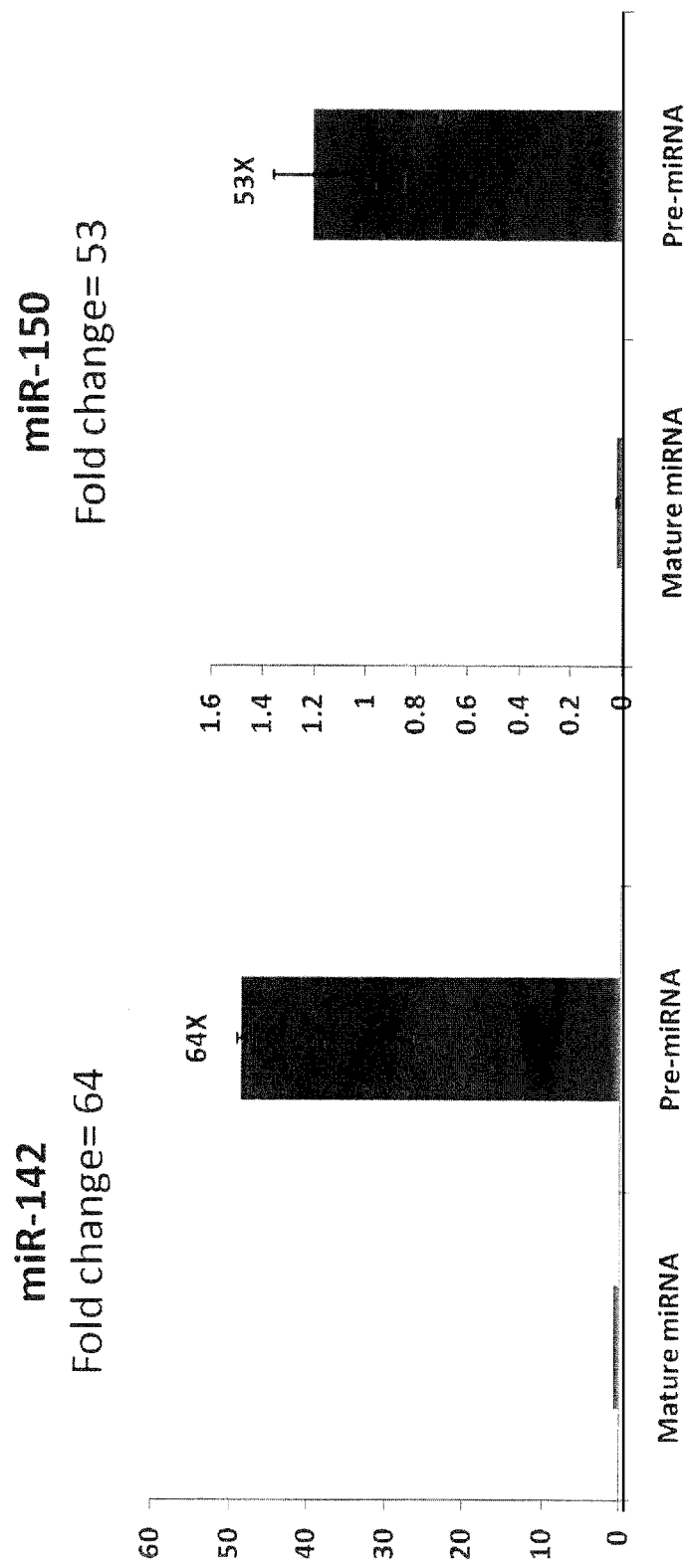
FIGS. 8A-B show that the UQmiR miRNA qPCR assay of the present invention discriminates mature miRNAs from pre-miRNAs. Mature miRNA-specific and pre-miRNA-specific PCR primers, which have extra sequences at the 3'-ends but no extra sequences at the 5'-ends, were used to detect pre-miRNA. A total of 7.85E8 copies of synthetic pre-miR-142 and pre-miR-150 were added to the RT reaction. The results show that mature miRNA-specific primers do not amply pre-miRNAs. The folds of discrimination are over 50 times. The Y axis represents fluorescence intensity corresponding to the specific amplification levels of the template.
Figure 9A:
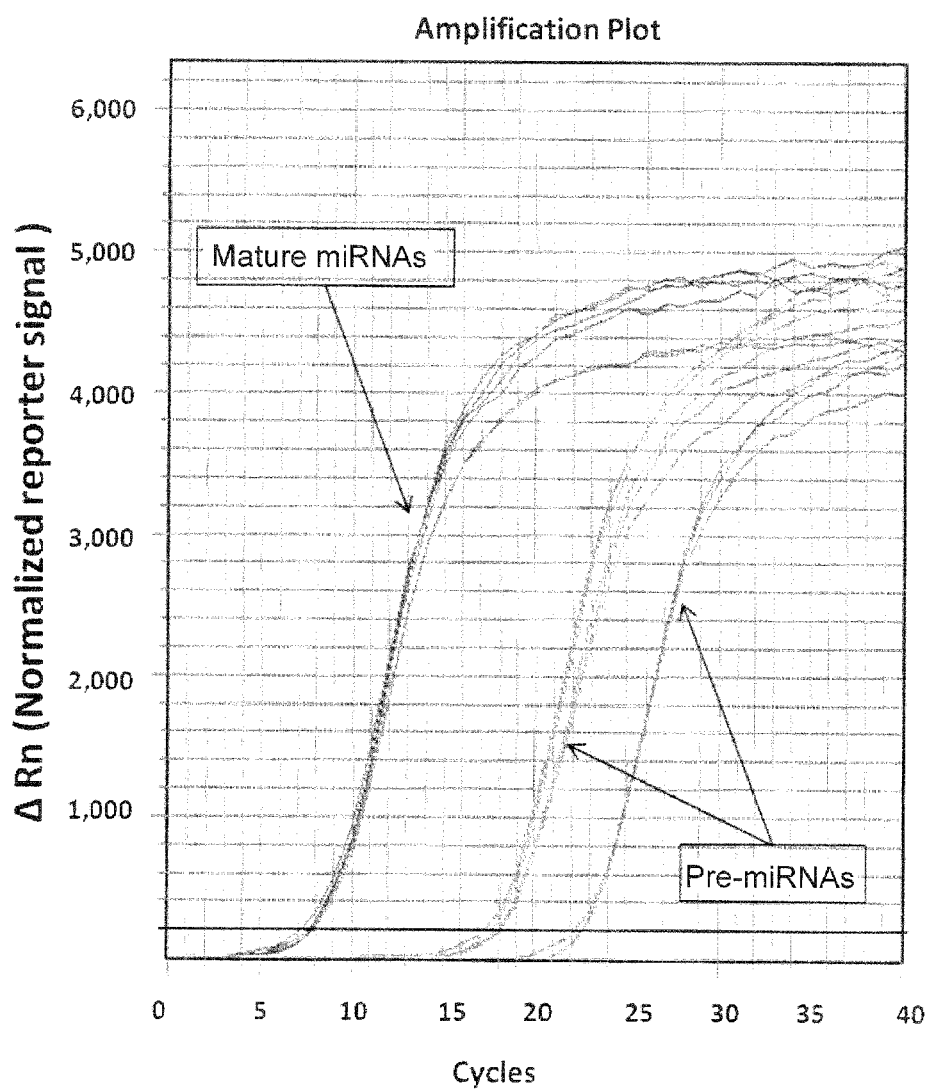
FIGS. 9A-C show that the UQmiR miRNA qPCR assay of the present invention discriminates mature miRNAs from pre-miRNAs. UQmiR primers consisting of sequences from mature miRNA and extra sequences that flank the mature miRNA sequences were used to detect mature miRNA and pre-miRNA sequences. A total of 7.85E8 copies of synthetic Let-7a, miR-142, pre-Let-7a, pre-miR-142 and pre-miR-150 were added to the RT reaction. The results show that mature miRNA-specific primers do not amply pre-miRNAs. The folds of discrimination are over one thousand times.
Figure 9B:
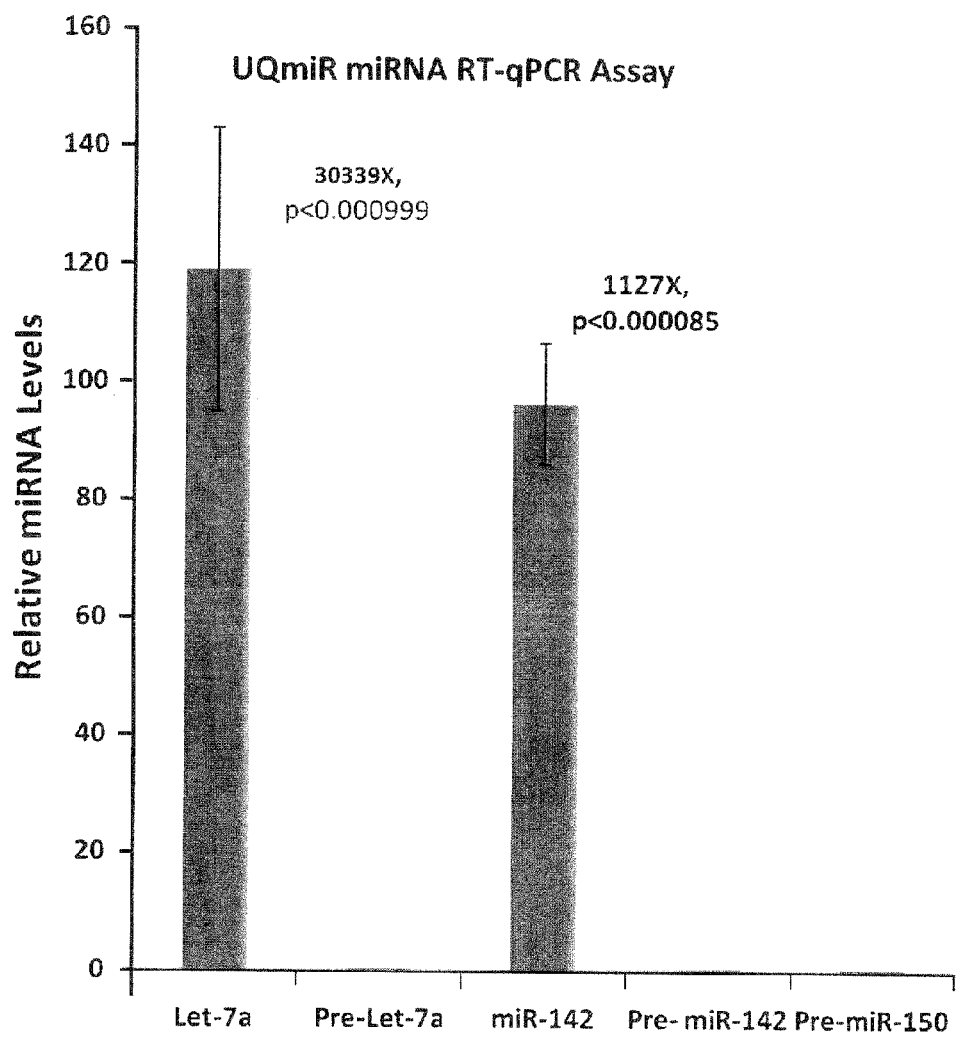
Figure 9C:
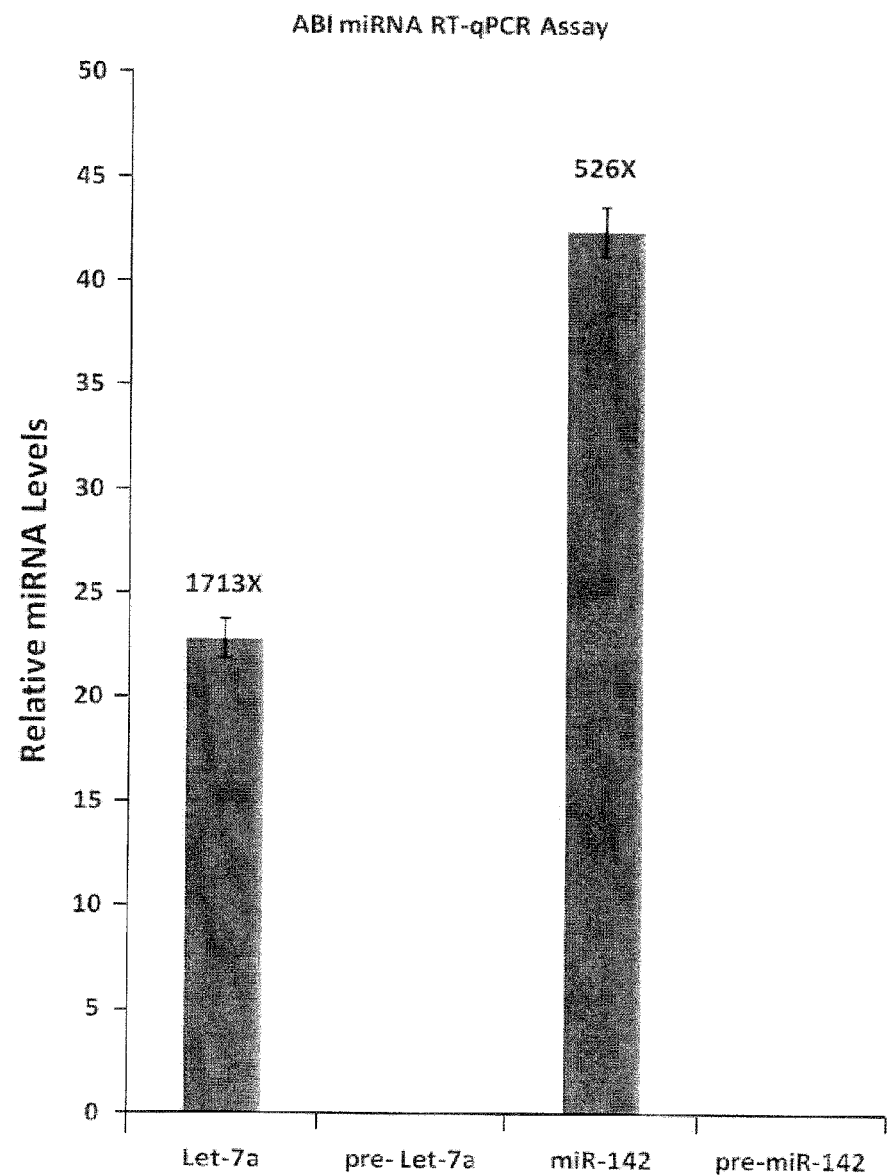

UQmiR primers that comprise extra sequences at the 3'-end of the miRNA sequence discriminate mature miRNAs over pre-miRNAs in 50 folds (FIG. 8A-B). UQmiR primers that comprise extra sequences at both 3'- and 5'-ends of the mature miRNA sequence discriminate mature miRNAs over pre-miRNAs over one thousand times; thus, the present miRNA assay is far more specific than the ABI miRNA Taqman assay (FIG. 9A-C).

Example 7

Specificity and Sensitivity of the UQmiR RT-QPCR Assay

FIG. 10 shows that the RT-qPCR miRNA Taqman assay (UQmiR) assay discriminates miRNAs within the mouse Let-7 miRNA family. The miRNA members of the same family are highly homologous and can differ from each other only in terms of a few bases. Also, the UQmiR miRNA qPCR assay is as sensitive as the commercially available Taqman assay (FIG. 12).

In addition, the UQmiR can sensitively detect plasma and serum miRNAs in clinical samples. FIG. 12 shows that the present miRNA assay sensitively and specifically detect 88 out of 94 miRNAs in 0.8 µl of plasma samples.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

All patents, patent applications, provisional applications, and publications referred to or cited herein, supra or infra, are incorporated by reference in their entirety, including all figures and tables, to the extent they are not inconsistent with the explicit teachings of this specification.

REFERENCES

C. M. Croce and G. A. Calin. 2005. miRNAs, cancer, and stein cell division. *Cell* 122(1): 6-7.

S. Griffiths-Jones, H. K. Saini, S. van Dongen and A. J. Enright. 2008. miRBase: tools for microRNA genomics. *Nucleic Acids Res* 36(Database issue): D154-8.

L. He and G. J. Hannon. 2004. MicroRNAs: small RNAs with a big role in gene regulation. *Nat Rev Genet* 5(7): 522-31.

I. Alvarez-Garcia and E. A. Miska. 2005. MicroRNA functions in animal development and human disease. *Development* 132(21): 4653-62.

H. Wang, R. A. Ach and B. Curry. 2007. Direct and sensitive miRNA profiling from low-input total RNA. *RNA* 13(1): 151-9.

J. W. Wang and J. Q. Cheng. 2008. A simple method for profiling miRNA expression. *Methods Mol Biol* 414: 183-90.

J. Shingara, K. Keiger, J. Shelton, W. Laosinchai-Wolf, P. Powers, R. Conrad, D. Brown and E. Labourier. 2005. An optimized isolation and labeling platform for accurate microRNA expression profiling. *RNA* 11(9): 1461-70.

P. T. Nelson, D. A. Baldwin, L. M. Scearce, J. C. Oberholtzer, J. W. Tobias and Z. Mourelatos. 2004. Microarray-based, high-throughput gene expression profiling of microRNAs. *Nat Methods* 1(2): 155-61.

J. Li, B. Yao, H. Huang, Z. Wang, C. Sun, Y. Fan, Q. Chang, S. Li, X. Wang and J. Xi. 2009. Real-time polymerase chain reaction microRNA detection based on enzymatic stem-loop probes ligation. *Anal Chem* 81(13): 5446-51.

E. Varkonyi-Gasic, R. Wu, M. Wood, E. F. Walton and R. P. Hellens. 2007. Protocol: a highly sensitive RT-PCR method for detection and quantification of microRNAs. *Plant Methods* 3: 12.

S. Ro, C. Park, J. Jin, K. M. Sanders and W. Yan. 2006. A PCR-based method for detection and quantification of small RNAs. *Biochem Biophys Res Commun* 351(3): 756-63.

C. Chen, D. A. Ridzon, A. J. Broomer, Z. Zhou, D. H. Lee, J. T. Nguyen, M. Barbisin, N. L. Xu, V. R. Mahuvakar, M. R. Andersen, K. Q. Lao, K. J. Livak and K. J. Guegler. 2005. Real-time quantification of microRNAs by stem-loop RT-PCR. *Nucleic Acids Res* 33(20): e179.

F. Tang, P. Hajkova, S. C. Barton, K. Lao and M. A. Surani. 2006. MicroRNA expression profiling of single whole embryonic stem cells. *Nucleic Acids Res* 34(2): e9.

We claim:

1. A composition of matter comprising a universal probe for detecting, quantifying and/or profiling miRNA, wherein the universal probe comprises a sequence that is, or basepairs with, at least part of the stem of a stem-looped universal adaptor sequence, wherein said universal probe comprises one or more locked nucleic acids and a detectable moiety, and wherein said sequence of said universal probe consists of ACC[A][T][C]A[A][T][C]G[T]G[T]G (SEQ ID NO: 16), wherein bracketed nucleotides are locked nucleic acids.

2. A probe comprising a sequence consisting of SEQ ID NO:16, wherein said probe comprises one or more locked nucleic acids.

3. The probe of claim 2, wherein said probe further comprises a detectable moiety.

4. The probe of claim 3, wherein said detectable moiety comprises a fluorophore.

5. The probe of claim 3, wherein said probe further comprises a quencher molecule attached to a first end of said sequence, and wherein said detectable moiety is a fluorescent dye attached to a second end of said sequence.

* * * * *